(12) United States Patent
Lyuboshenko

(10) Patent No.: US 10,261,302 B1
(45) Date of Patent: Apr. 16, 2019

(54) SAMPLE HOLDER FOR MICROSCOPY

(71) Applicant: Igor Lyuboshenko, Le Plessis-Robinson (FR)

(72) Inventor: Igor Lyuboshenko, Le Plessis-Robinson (FR)

( * ) Notice: Subject to any disclaimer, the term of this patent is extended or adjusted under 35 U.S.C. 154(b) by 0 days.

(21) Appl. No.: 15/680,079

(22) Filed: Aug. 17, 2017

Related U.S. Application Data

(60) Provisional application No. 62/489,168, filed on Apr. 24, 2017.

(51) Int. Cl.
*G02B 21/26* (2006.01)
*G02B 21/06* (2006.01)

(52) U.S. Cl.
CPC .............. *G02B 21/26* (2013.01); *G02B 21/06* (2013.01)

(58) Field of Classification Search
CPC .. G02B 21/00; G02B 21/0004; G02B 21/002; G02B 21/0024; G02B 21/0032; G02B 21/0036; G02B 21/0052; G02B 21/006; G02B 21/0076; G02B 21/06; G02B 21/082; G02B 21/086; G02B 21/088; G02B 21/16; G02B 21/18; G02B 21/24; G02B 21/36; G02B 21/361
USPC ........ 359/362, 363, 368, 369, 381, 385, 388, 359/390
See application file for complete search history.

(56) References Cited

U.S. PATENT DOCUMENTS

| | | |
|---|---|---|
| 7,554,725 B2 | 6/2009 | Stelzer |
| 7,787,179 B2 | 8/2010 | Lippert |
| 8,482,854 B2 * | 7/2013 | Lippert ................. G02B 21/33 359/381 |
| 8,699,133 B2 | 4/2014 | Lippert |
| RE45,575 E | 6/2015 | Lippert |
| 9,316,824 B2 | 4/2016 | Shroff |
| 9,404,869 B2 | 8/2016 | Keller |
| 9,587,213 B2 * | 3/2017 | Morgan ............... C12N 5/0012 |
| 2012/0282667 A1 * | 11/2012 | Lippert ................. G02B 21/34 435/174 |
| 2014/0202265 A1 | 7/2014 | Hellmich et al. |
| 2015/0098126 A1 | 4/2015 | Keller |
| 2016/0214107 A1 | 7/2016 | Viasnoff |

(Continued)

FOREIGN PATENT DOCUMENTS

WO 20160178856 W 11/2016
WO 2017062741 A1 4/2017

OTHER PUBLICATIONS

Chmielewski et al., "Fast imaging of live organisms with sculpted light sheets", Scientific Reports, Apr. 20, 2015.

(Continued)

*Primary Examiner* — Arnel C Lavarias
(74) *Attorney, Agent, or Firm* — Van Pelt, Yi & James LLP

(57) ABSTRACT

A system for holding a sample for a microscope includes a first container with a substantially transparent wall, and a second container formed from a substantially transparent embedding medium molded on a mounting. The second container is configured to enclose the sample and at least a portion of the second container is positioned within the first container. The second container is configured to be rotated at least in part within the first container about a rotational axis and configured to be placed within a detection optical path of an optical detection axis of the microscope.

20 Claims, 25 Drawing Sheets

(56) References Cited

U.S. PATENT DOCUMENTS

| | | |
|---|---|---|
| 2016/0241758 A1 | 8/2016 | Dohi |
| 2018/0164569 A1 | 6/2018 | Brinkman |
| 2018/0275389 A1 | 9/2018 | Shepherd |

OTHER PUBLICATIONS

Fahrbach et al., "Rapid 3D light-sheet microscopy with a tunable lens", Optics Express, vol. 21, No. 18, p. 21010-21026, Aug. 30, 2013.

Hedde et al., "Selective plane illumination microscopy with a light sheet of uniform thickness formed by an electrically tunable lens", from Microscopy research and technique, Jun. 24, 2016.

Hedde et al., "sideSPIM—selective plane illumination based on a conventional inverted microscope", from Biomedical Optics Express, vol. 8, No. 9, p. 3918-3937, Aug. 1, 2017.

Jan Huisken et al., "Selective Plane Illumination Microscopy", In: "Handbook of Biological Confocal Microscopy", Jan. 1, 2006, Springer, New York, NY. pp. 672-675.

Per Niklas Hedde et al., "Selective plane illumination microscopy with a light sheet of uniform thickness formed by an electrically tunable lens", Microscopy Research and Technique, vol. 81, No. 9, Jun. 24, 2016, pp. 924-928.

\* cited by examiner

SECTION A-A        SECTION C-C

SAMPLE HOLDER FOR MICROSCOPY

CROSS REFERENCE TO OTHER APPLICATIONS

This application claims priority to U.S. Provisional Patent Application No. 62/489,168 entitled EXTENDING OPTICAL MICROSCOPES TO PROVIDE SELECTIVE PLANE ILLUMINATION MICROSCOPY filed Apr. 24, 2017 which is incorporated herein by reference for all purposes.

BACKGROUND OF THE INVENTION

Light sheet fluorescence microscopy or selective plane illumination microscopy (SPIM) technology typically relies on illuminating a sample in thin optical slices, formed from laser light, exciting the fluorophores in the sample and acquiring light emitted by the illuminated plane inside the sample. The direction in which the light is detected is typically perpendicular to the illuminated plane.

With SPIM, the lateral resolution is determined by the detection objective lens and the axial resolution is related to the numerical aperture (NA) of the illumination objective. With low NAs, the Z resolution is determined by the thickness of the light sheet, with an excellent isotropic Point Spread Function. With higher NAs, the axial resolution is similar to confocal fluorescence microscopes. Images from light sheet microscopes exhibit a better signal-to-noise (S/N) ratio and a higher dynamic range than images produced by confocal fluorescence microscopes.

Typically, standalone light sheet fluorescence microscopes are costly and take up a considerable amount of valuable physical space in a laboratory. Additionally, current techniques to hold samples for SPIM limit the type and range of samples that can be observed using SPIM.

BRIEF DESCRIPTION OF THE DRAWINGS

Various embodiments of the invention are disclosed in the following detailed description and the accompanying drawings.

DETAILED DESCRIPTION

Figure 1A:
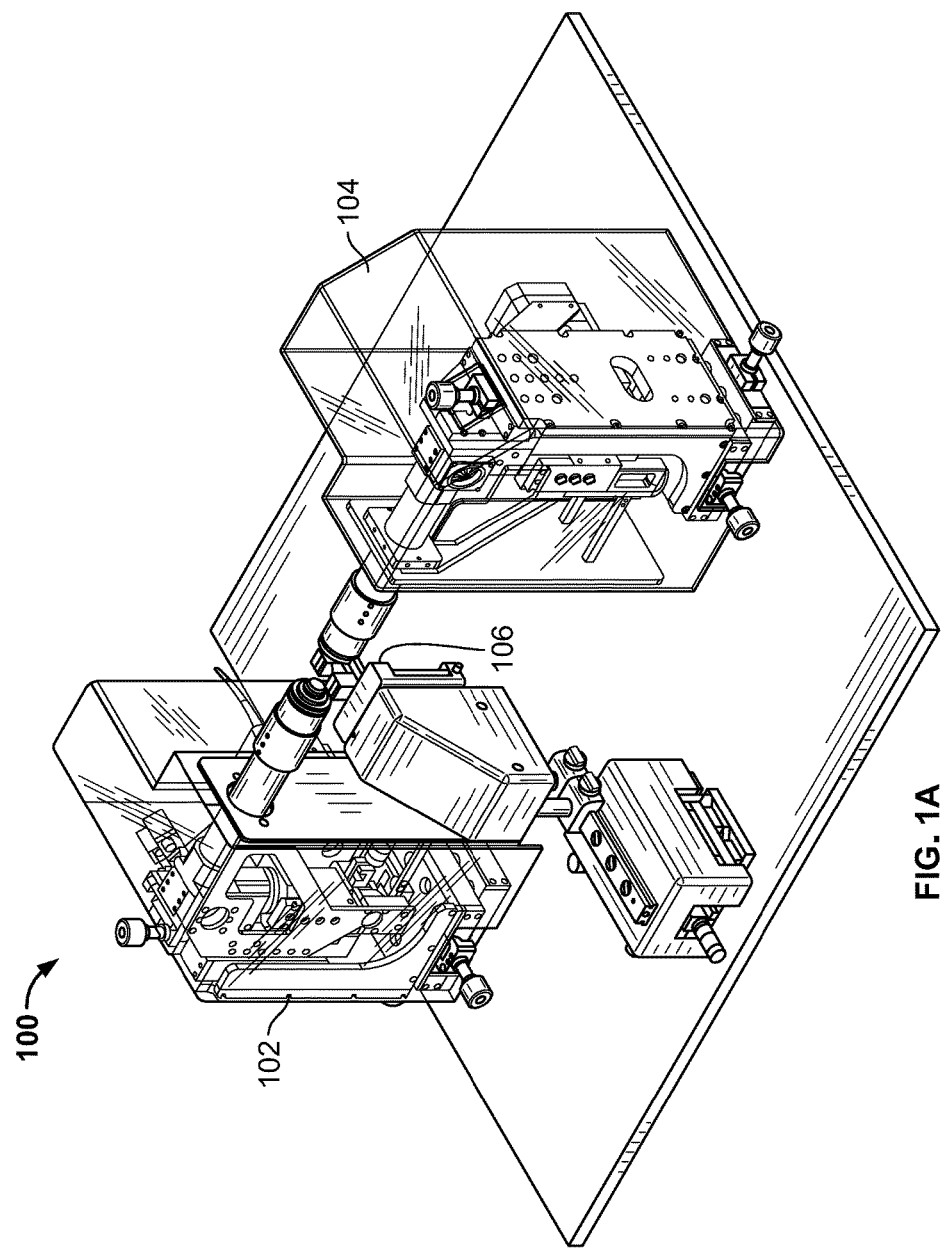
FIG. 1A is a diagram illustrating an embodiment of components of a system that can be coupled to a vertical microscope to convert the vertical microscope to perform SPIM.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Typical SPIM solutions are offered as stand-alone digital systems with a far different operating approach than conventional optical microscopy. Using traditional SPIM microscopes requires special training and imposes new behaviors upon the users, thus minimizing their productivity and limiting the market penetration and scientific community's awareness of advantages offered by the light sheet technology.

A system for converting a vertical optical microscope (e.g., upright or inverted microscope) to provide selective plane illumination microscopy is disclosed. For example, by adding components to a traditional vertical optical microscope to convert it to provide selective plane illumination microscopy, cost saving and reduced physical size footprint are achieved as compared to using a traditional dedicated standalone in SPIM microscope. For example, a typical lab setting already includes a traditional vertical optical microscope and allowing the traditional vertical optical microscope to be converted to an SPIM microscope saves costs and space. An illumination source is configured to generate a light sheet along a longitudinal axis to illuminate a sample placed in a vertical optical detection axis of the vertical optical microscope. The illumination source is configured to generate a light sheet along a longitudinal axis that is substantially perpendicular to a vertical optical detection axis of the vertical optical microscope and the illumination source is configured to produce an excitation at a plane in the sample that generates fluorescent emissions. A detection sensor is placed in the detection optical path of the vertical optical detection axis of the vertical optical microscope. The detection sensor is configured to detect the fluorescent emissions to provide selective plane illumination microscopy.

Typical standalone SPIM microscopes are configured in a horizontal orientation. For example, both the illumination path and the detection path are oriented horizontally (e.g., in the horizontal plane substantially perpendicular to the direction of gravity). For example, typical solutions include an excitation illumination source objective having the excitation illumination axis and the detection objective having the detection optical axis that are both engaged to the same mount body, where the two axes are oriented in a perpendicular relation to each other in the horizontal plane. This often is due to limitations in traditional sample holding solutions. For example, SPIM is often utilized to observe biological samples suspended in a fluid and limitations how the sample can be contained and rotated using traditional sample holding solutions require the sample to be illuminated and detected in the horizontal plane. However, the detection optical path of traditional vertical optical microscopes is in the vertical direction. Solutions described herein allow SPIM detection to be achieved using the vertical optical microscope's optical arrangement in the vertical direction.

In some embodiments, both observation and acquisition modes are added to the microscope detection objective's optical arrangement of vertical optical microscopes. By using the microscope stand of the vertical optical microscope as an integral part of the detection unit, it takes advantage of quality optical elements already present in the detection path (e.g., including objective turret, filter wheel, binoculars, and video port), thereby reducing complexity of building a selective plane illumination microscopy system. As no alterations to the detection path's optics of the vertical optical microscope are introduced, all other functionalities that could be necessary for other observation modes (e.g., transmission, wide field fluorescence, etc.) are kept unaltered, including convenient means for specific applications such as electrophysiology. Therefore it serves as an upgrade on existing microscopy platforms by adding light sheet imaging capabilities providing a cost effective solution or as a whole system by integrating a functional fluorescence microscope.

FIG. 1A is a diagram illustrating an embodiment of components of a system that can be coupled to a vertical microscope to convert the vertical microscope to perform SPIM. System 100 includes illumination units 102 and 104, and stepper stage 106.

Illumination units 102 and 104 are designed to work with a laser source (e.g., fibered laser source) to produce a light sheet using a cylindrical lens. This allows direct imaging of an optical section with a single frame at full camera resolution. For better illumination plane homogeneity across the specimen, two illumination units are used on both sides of a sample to compensate the absorption effects with a thick specimen. In some embodiments, the light sheet is projected using a standard finite-infinite objective, which can be adapted according to sample size and detection magnification. The illumination units are designed to compensate chromatic shift for the visible spectrum, thus allowing the simultaneous illumination at several wavelengths using a laser combiner for multi-fluorescence imaging. Although two illumination units are shown, a single or any other number of illumination units may be utilized in various other embodiments. In some embodiments, illumination units 102 and/or 104 produce a pencil beam rather than or in addition to a light sheet.

Stepper stage 106 includes a motorized translation stage to move the sample through the illumination plane of illumination units 102 and 104. Thus, using stepper stage 106, the position of the illumination sheet and the detection plane may remain in fixed position while detecting various slices as the translation stage is moved in steps. The shown stepper stage 106 includes a support for a sample chamber, a z-stage that is moveable in the vertical z-direction via a motor, a slider, and controls for x and y position adjustments of the stage in the horizontal plane. In some embodiments, a base configured to engage a sample stage for supporting and orienting the sample holder in an x-y direction is utilized. In some embodiments, a translational stage configured to engage the sample holder in the z-direction is utilized.

Figure 1B:
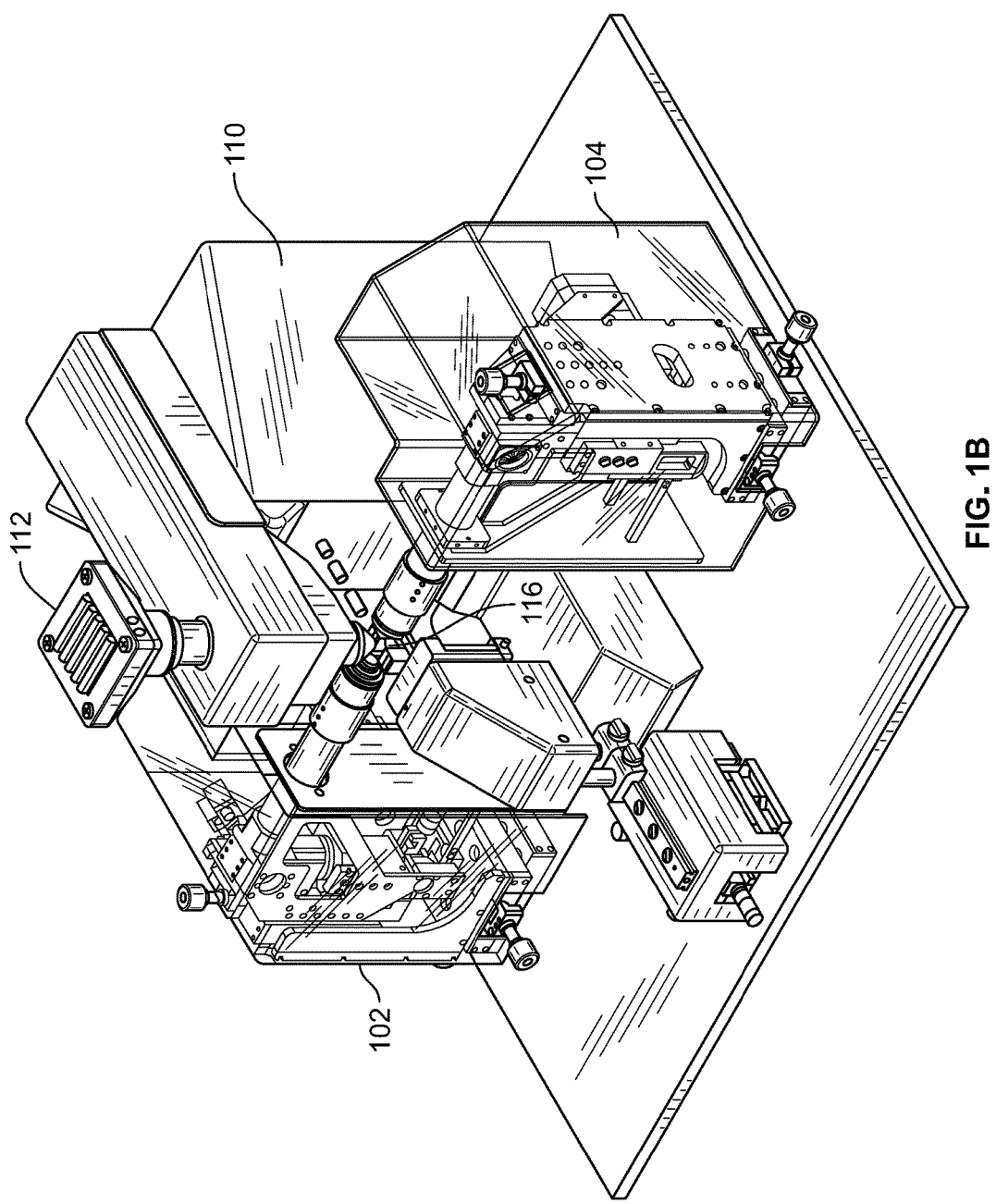
FIG. 1B is a diagram illustrating an embodiment showing an add-on system added to a vertical microscope to convert the vertical microscope to perform SPIM.

FIG. 1B is a diagram illustrating an embodiment showing an add-on system added to a vertical microscope to convert the vertical microscope to perform SPIM. For example, system 100 of FIG. 1A is shown engaged with vertical optical microscope 110. Vertical optical microscope 110 shown in this example is a trinocular fluorescence microscope equipped with a filter wheel and an objective turret with a water dipping/immersion detection lens. However in various other embodiments, other types of optical microscopes may be utilized. The optical detection path of optical microscope 110 utilized to perform SPIM may utilize components of microscope 110, including its components in the optical detection path (e.g., objective lenses, arm, filter in filter wheel, etc.). An output port of optical microscope 110 is coupled to detection unit 112 that is utilized to acquire the SPIM image detected using the optical detection path of microscope 110. For example, detection unit 112 includes a digital camera.

Sample chamber and holder assembly 116 has been configured to handle SPIM using a vertical optical detection path configuration as compared to traditional holders that have been designed to be utilized for horizontal optical SPIM detection paths. Sample chamber and holder 116 allows a sample to be rotated about a substantially horizontal rotational axis and substantially perpendicular to the optical axis of the detection objective using a rotational drive or knob. For example, sample chamber and holder assembly 116 embeds a sample in a substantially rigid substantially transparent embedding compound maintained in an immersion liquid and placed in the holder, allowing the sample to be rotated about the substantially horizontal rotational axis that is substantially perpendicular to the optical axis of the detection objective. In some embodiments, sample chamber and holder assembly 116 is supported by a sample stage for supporting and orienting assembly 116 in an x-y direction and/or a translational stage configured to engage the assembly 116 in the z-direction.

Figure 2:
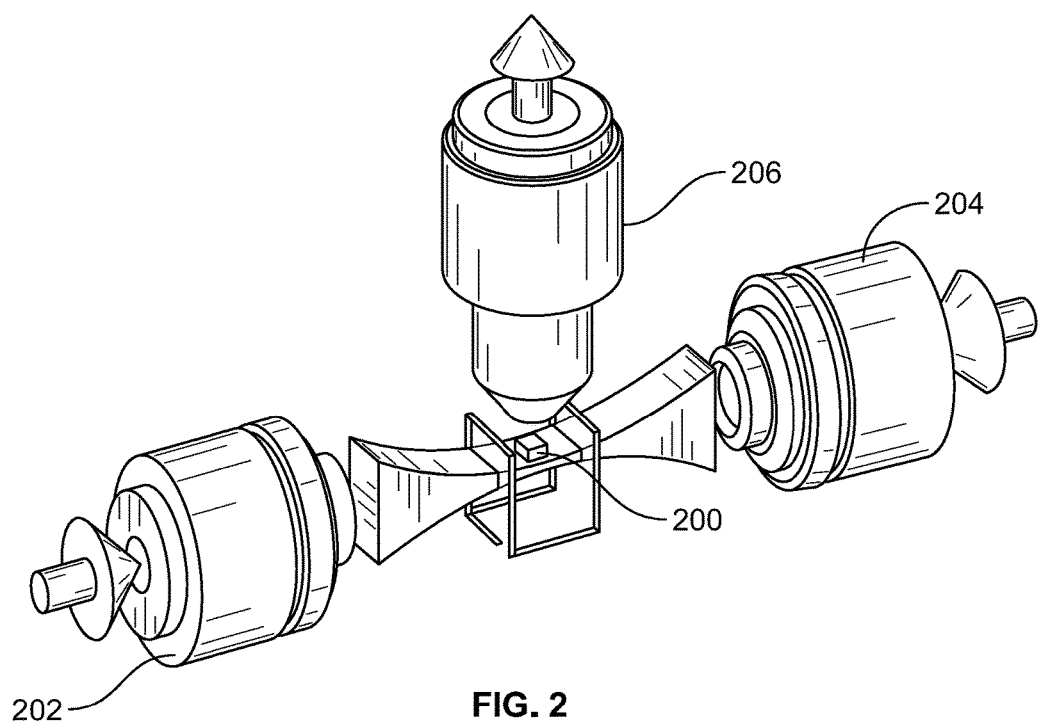
FIG. 2 is a diagram illustrating an example of illumination of a sample.

FIG. 2 is a diagram illustrating an example of illumination of a sample. Sample 200 is being illuminated by illumination objective 202 and illumination objective 204. The illuminated sample is observed via optical detection objective 206. In some embodiments, detection objective 206 is a part of microscope 110, illumination objective 202 is a part of illumination unit 102, and illumination objective 204 is a part of illumination unit 104 of system 100 of FIGS. 1A and 1B. For example, the illumination units are designed to work with fibered laser sources to produce a light sheet using cylindrical lenses of the objectives. This allows direct imaging of an optical section with a single frame at full camera resolution. For better illumination plane homogeneity across the specimen, two illumination units are used on both sides of the sample to compensate the absorption effects of a thick specimen sample. In some embodiments, the light sheet is projected using finite-infinite objectives, which can be adapted according to sample size and detection magnification. In some embodiments, the illumination output of the objectives has a cross section of an elongated ellipse due to an assembly of optical elements in which the thin sheet of light is generated from one or many laser light sources. In another embodiment, the illumination output of the objectives has a cross section of an elongated rectangle. Lenses of objectives 202 and 204 are designed to optically compensate chromatic shift for the visible spectrum, thus allowing the simultaneous illumination at several wavelengths using a laser combiner for multi-fluorescence imaging.

Illumination objectives 202 and 204 focus the laser light source to create a light sheet. However, as shown in in FIG. 2, due to the focusing of the light source by the lens of the objective, the light sheet is thinner at the focal point area (i.e., at the "waist") and becomes thicker away from the focal point area. A thinner light sheet allows for better image resolution and thus a uniformly thin light sheet is desired. Given the effects of the shown divergence, a light sheet within a limited range of thickness can be utilized in order to maintain a desired image resolution, thus limiting the field of view to the area of the light sheet within the thickness limit. However is some cases it may be desirable to capture a sample that is larger than the limited field of view. In some embodiments, a variable focus lens is utilized in one or more of the illumination objectives to sweep the focal point across the sample to create a thin light sheet over a larger area of the light sheet. For example, focus distance of the illumination lens is automatically adjusted to move the focus of the lens across the width of the sample during image capture to sweep the thinnest point of the light sheet across the width of the sample, allowing a larger field of view without physically moving the sample within the plane of the light sheet. The focus distance of the illumination lens may be adjusted mechanically. In some embodiments, rather than relying on the mechanical motor mechanism that may introduce vibrations, the focusing distance of the illumination lens may be changed electrically (e.g., via an electrically tunable lens that changes focus via electromagnets, piezoelectric element, current through a solution, etc.) without a use of a motor.

FIG. 3A-FIG. 3E are diagrams illustrating various embodiments of focusing unit add-ons to an optical microscope. High spatial and temporal resolution for a 3D light sheet imaging allows observation of physiological processes of living specimen while keeping them in their natural state without perturbation. Typical methods based on mechanical motion of the sample for volume acquisition introduce vibrations during the acquisition and limit the scanning speed. As water-dipping objectives are customarily used for observation of biologic samples in the samples' natural medium, perturbations from a moving detection objective may influence the sample behavior under observation and restrain the scope of application for dynamic studies. Larger specimens can also exceed the laser waist (focus) area and reduce the optical sectioning power of the light sheet assembly. In some embodiments, fast and vibration free 3D acquisition is performed using tunable lenses. For example, in order to generate a 3D image of a sample using SPIM, each slice of the sample at different depths is illuminated using a light sheet and captured using a lens focused on the slice. The image of the sample at different depths then can be digitally processed and combined to generate a 3D rendering of the sample. One way to capture the various slices of the sample at different depths is to physically move the sample up and down and/or side to side in increments. However as discussed previously, vibrations introduced in physically moving the sample may lead to drawbacks.

In some embodiments, instead of moving the sample for scanning the depth of the sample, a scanning device based on lens of dynamically variable focal distance is utilized. Video output focusing unit 302 may be inserted into the detection path between a microscope's video output port and a digital camera, and detection objective output focusing unit 320 may be inserted between the microscope's detection objective and the microscope turret and/or tube lens. One or both of focusing unit 302 and focusing unit 320 may be utilized in various embodiments.

The specimen sample (e.g., in its chamber) is set in a fixed position when the illumination plane (e.g., illumination source is physically moved up and down) and the detection plane move simultaneously through the sample automatically in sync. The detection plane may be moved by varying the vertical focusing distance of the lens of a focusing unit. The focusing distance of the focusing units may be changed mechanically. In some embodiments, rather than relying on a mechanical motor mechanism that may introduce vibrations, the focusing distance of a focusing unit may be changed electrically (e.g., via an electrically tunable lens that changes focus via electromagnets, piezoelectric element, current through a solution, etc.) without a use of a motor. As the sample remains in a steady position, vibrations and perturbation issues are alleviated. Incidental specimen mounting and holding becomes much easier. Additionally, if a wider field of view of the sample is desired, the horizontal sweeping of the "waist" focus of the light sheet as previously discussed may be used in conjunction with vertical variable focus. This allows the acquisition of images in the light sheet mode where the image of the portion of the sample being acquired is automatically focused on the thinnest area of the laser beam being swept vertically and horizontally. Hence, it provides the sharpest optical sectioning in the whole frame, greatly reducing shadows occurring within the observed sample. By integrating these scanning means, the light sheet system not only provides optical sectioning with optimal spatial resolution and signal to noise ratio, but also delivers unprecedented temporal resolution for 3D acquisition, addressing the needs for dynamic imaging of rapid biophysical processes.

Figure 3A:
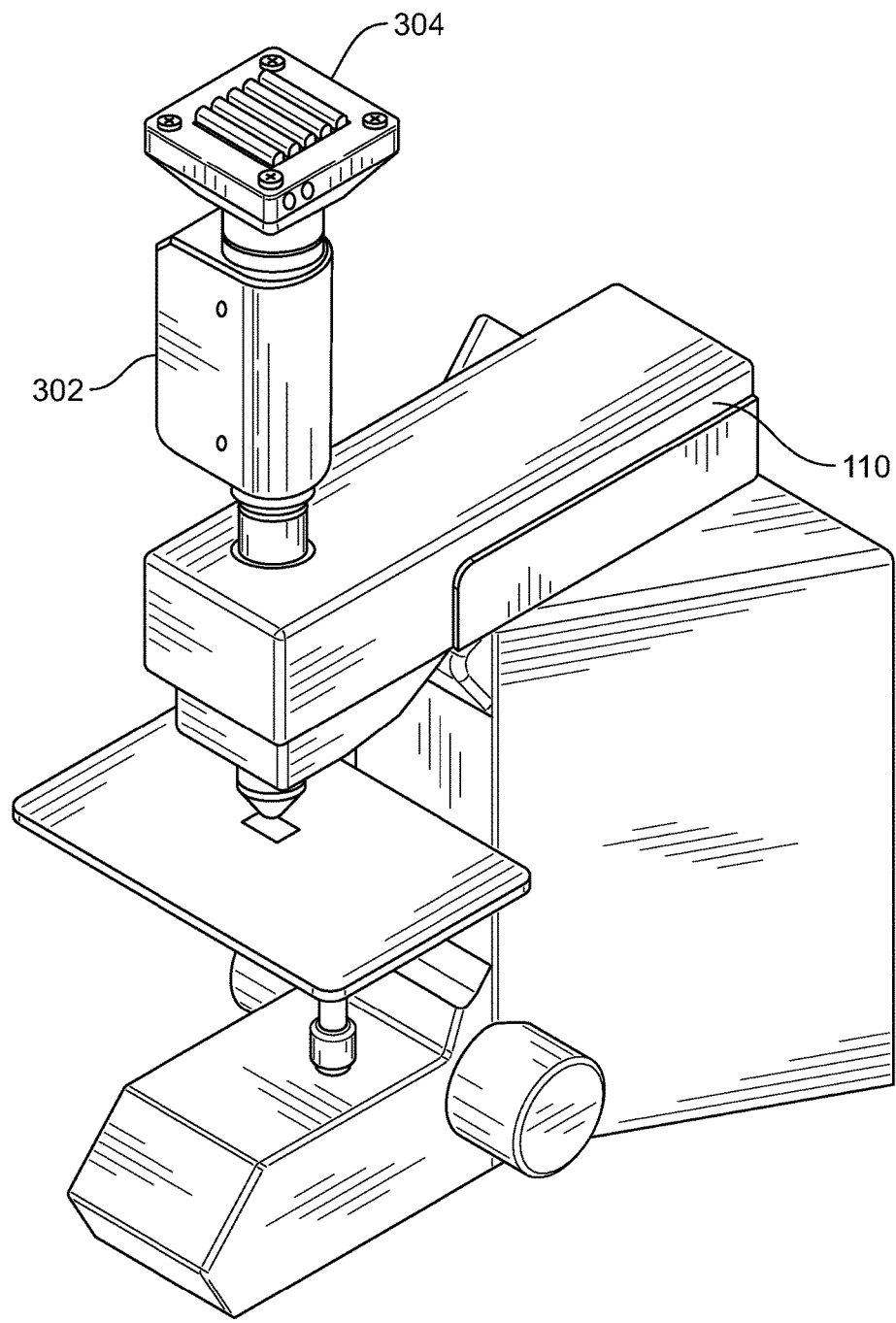
FIG. 3A-FIG. 3E are diagrams illustrating various embodiments of focusing unit add-ons to an optical microscope.
Figure 3B:
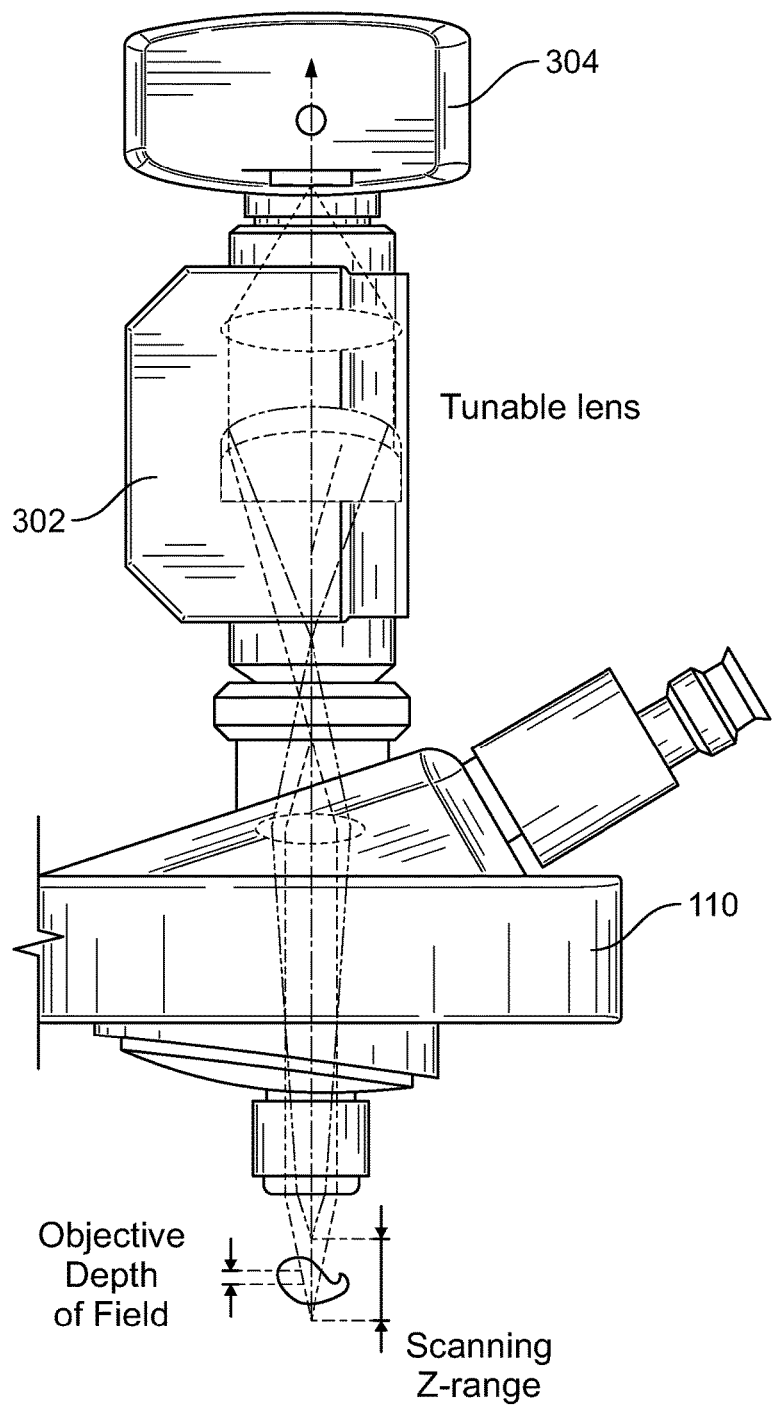
Figure 3C:
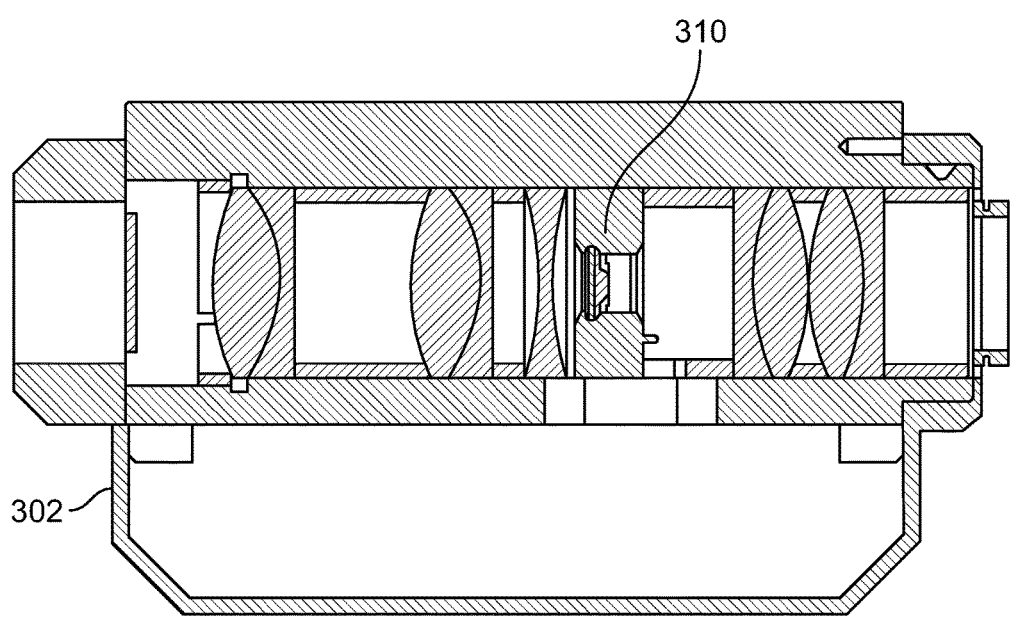

FIG. 3A-FIG. 3C are diagrams illustrating an embodiment of a video output focusing unit add-on to an optical microscope. Video output focusing unit 302 is coupled to a video output port (e.g., C-Mount interface) of optical microscope 110 and an optical input of digital camera 304 (e.g., via screw-threaded, press fit, friction, locking, bayonet, or any other types connecting/mounting interfaces). For example, focusing unit 302 is included in and/or coupled to detection unit 112 of FIG. 1B. Digital camera 304 is coupled to focusing unit 302 and digital camera 304 captures an image of a sample obtained via an optical path of lenses of focusing unit 302 added to the optical detection path of microscope 110. Focusing unit 302 has an optical axis that is substantially parallel to the optical axis of the detection objective of the optical microscope for manual or automatic focusing onto the same geometrical plane substantially perpendicular to the optical axis of the detection objective of the optical microscope, which is illuminated by the light generated by one or more illumination sources. Focusing unit 302 includes an arrangement of optical elements with at least one optical element that is able to dynamically change focal distance (e.g., tunable lens 310). FIG. 3C shows an internal cutaway view of focusing unit 302. Tunable lens 310 is able to change its focusing distance electrically (e.g., via electromagnets, piezoelectric element, current through a solution, etc.) without a use of a motor. In other embodiments, focusing distance of focusing unit 302 may be changed mechanically.

Figure 3D:
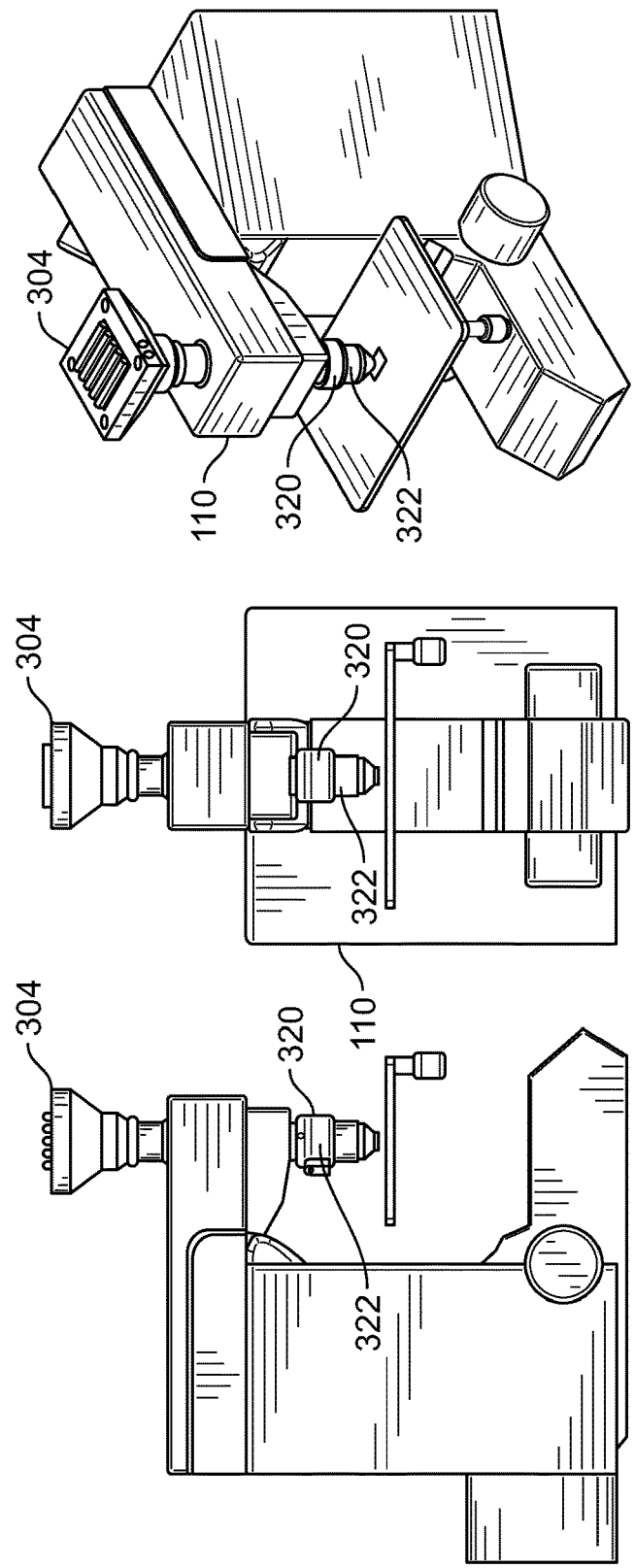
Figure 3E:
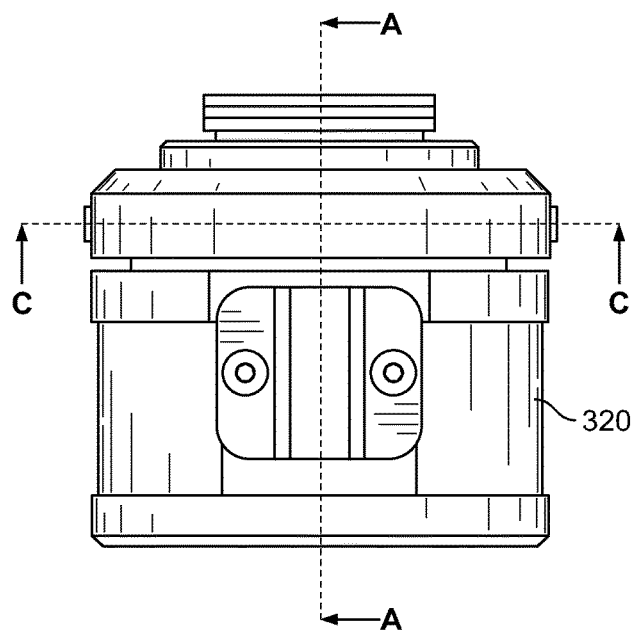
Figure 3E:
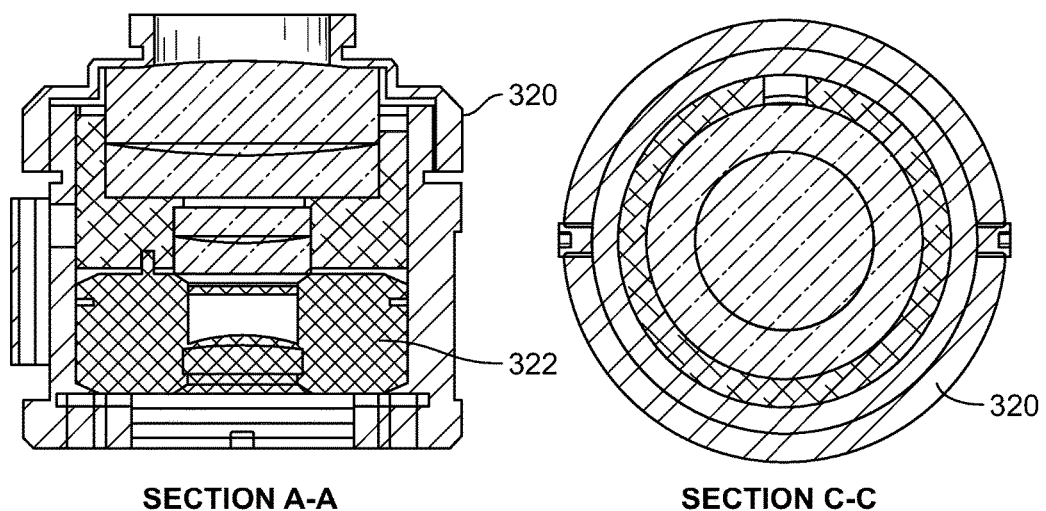

FIG. 3D-FIG. 3E are diagrams illustrating an embodiment of a detection objective output focusing unit add-on to an optical microscope. Detection objective output focusing unit 320 is directly coupled to detection objective 322 and the microscope turret and/or tube lens of optical microscope 110 (e.g., via screw-threaded, press fit, friction, locking, bayonet, or any other types connecting/mounting interfaces). For example, focusing unit 320 functions an intermediary optical element between optical detection objective 322 and a microscope turret of optical microscope 110. Digital camera 304 is coupled to focusing unit 320 and digital camera 304 captures an image of a sample obtained via an optical path of lenses of focusing unit 320 added to the optical detection path of microscope 110. Focusing unit 320 has an optical axis that is substantially parallel to the optical axis of the detection objective of the optical microscope for manual or automatic focusing onto the same geometrical plane substantially perpendicular to the optical axis of the detection objective of the optical microscope, which is illuminated by the light generated by one or more illumination sources. Focusing unit 320 includes an arrangement of optical elements with at least one optical element that is able to dynamically change focal distance (e.g., tunable lens 322). FIG. 3E shows an external side view and various internal cutaway views of focusing unit 320. Tunable lens 322 is able to change its focusing distance electrically (e.g., via electromagnets, piezoelectric element, current through a solution, etc.) without a use of a motor. In other embodiments, focusing distance of focusing unit 320 may be changed mechanically.

Figure 4:
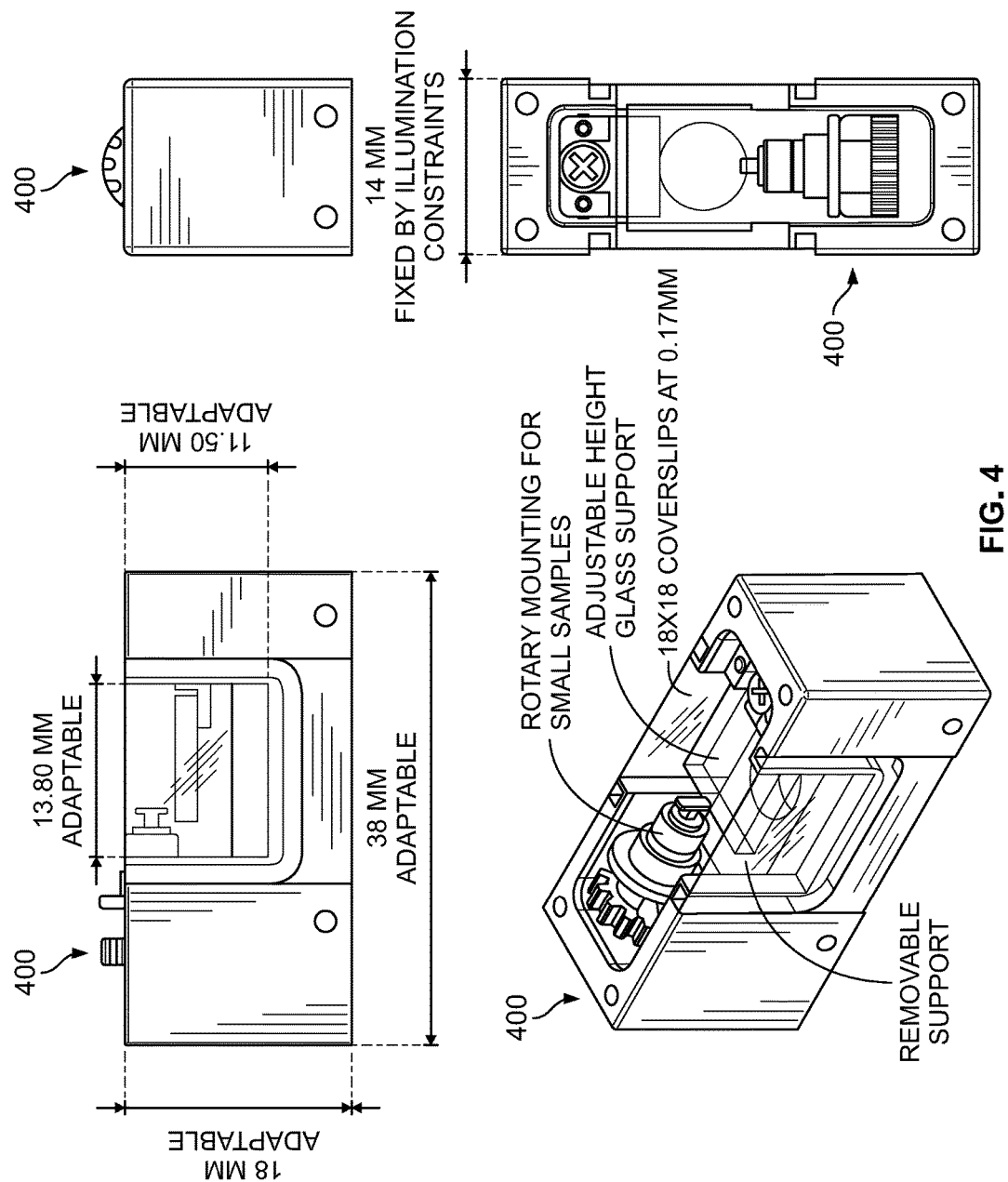
FIG. 4 is a diagram illustrating an embodiment of a sample holding chamber assembly.

FIG. 4 is a diagram illustrating an embodiment of a sample holding chamber assembly. FIG. 4 shows various different view angles of sample chamber assembly 400. An example of sample chamber assembly 400 is sample chamber and holder assembly 116 in FIG. 1B.

In typical SPIM systems, the sample is held in a container that is observed horizontally due to the potential deformability of the sample embedding medium as a result of action of gravitational force. This is because the optical axis of the detection lens of the microscope cannot extend vertically, as it does in the conventional configuration of the majority of upright or inverted optical microscopes. However, a vast majority of the conventional vertical (e.g., upright or inverted) microscopes have detection objective's optical axes extending vertically. Thus, conventional sample holding systems for SPIM often cannot be utilized in these vertical microscopes. Therefore, there is a need both in providing chambers that are filled with immersion medium and that can be used in conventional vertical microscopes, comprising an open top yielding unhindered access to both air and immersion objectives, substantially transparent bottom side for viewing the samples in transmission mode, and designed to be easily removable from the microscope's stand for the microscope to retrieve its original, for example wide field, functional configuration.

Sample chamber assembly 400 includes a chamber that is enclosed on the sides and bottom but open on the top (allowing a direct medium immersion for a detection objective). The bottom of the chamber is substantially transparent for observation in transmission mode and coarse sample positioning. Two of the sides include substantially transparent coverslips that allow a light sheet to pass through to illuminate a sample placed in the chamber. In some embodiments, the sample is placed in the chamber of sample chamber assembly 400 on a height adjustable (e.g., by turning a pin/screw/knob) glass support. The glass support may be removed from the chamber (or moved away) and a rotary mounting (e.g., T-spike holder) coupled to a cylindrical sample holder holding a sample may be placed in the chamber. The rotary mounting coupled to a cylindrical sample holder can be laid horizontally in the chamber and the sample can be rotated about a horizontal axis by rotating a knob and/or via gears that are coupled to a rotating mechanism (e.g., may be motorized). For example, a sample is embedded in a substantially rigid cylindrical transparent embedding compound maintained in an immersion liquid and placed in a rotary mount coupled to the chamber. The rotary mount allows a rotational movement of the sample using a rotational drive or knob about a substantially horizontal rotational axis and substantially perpendicular to the optical axis of the detection objective.

In some embodiments, the chamber of assembly 400 is filled with an immersion solution. For example, the chamber that includes a sample (e.g., either on a glass support or in a cylindrical sample holder) is filled with a saline solution, allowing the use of water dipping/immersion objectives. In some embodiments, to ensure better resistance against various corrosive agents such as salt water or clearing agents and ease cleaning/sonicating/autoclaving, non-transparent parts of chamber assembly 400 are to be made from medical grade and Polytetrafluoroethylene (e.g., Teflon) parts, suited to be used together with temperature control equipment for precise temperature control and equipped with nozzles that allow constant carbon dioxide control during experimentation by flowing carbon dioxide on the top of the chamber. For precise temperature control throughout an experiment, the baseplate of the chamber is configured for temperature control. This allows transmission of heating/cooling via contact with a liquid circulation interface for temperature control (e.g., allowing temperature control from 15° C. to 37° C.). Carbon dioxide control is achieved through nozzles that allow a desired carbon dioxide flow on the top of the chamber.

Figure 5:
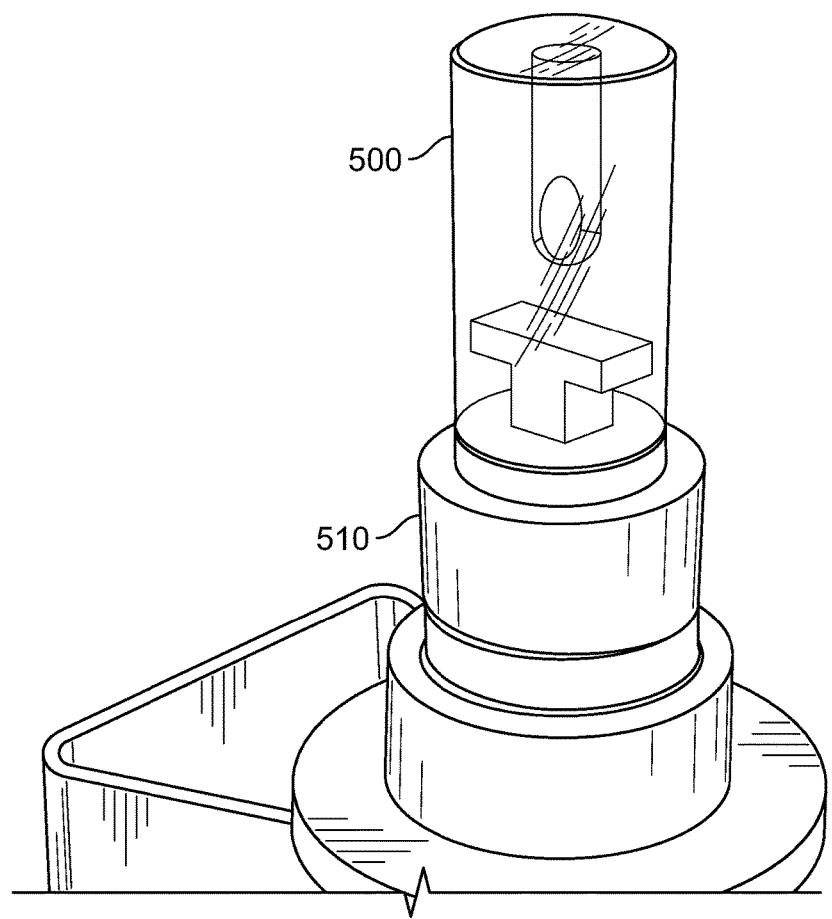
FIG. 5 is a diagram illustrating an embodiment of a mold-formed sample holder over a T-spike rotary mounting.

FIG. 5 is a diagram illustrating an embodiment of a mold-formed sample holder over a T-spike rotary mounting. In some embodiments, sample holder 500 is placed horizontally in the chamber of chamber assembly 400 shown in FIG. 4 for observation of the included sample via SPIM performed using the system shown in FIG. 1B. Using the conventional upright or inversed microscope's objective arrangement as a detection path of the selective plane light sheet system may require the sample to be rotated about its horizontal axis. In some embodiments, a sample is embedded in an embedding medium with an increased rigidity sufficient to withstand the actions of gravitational forces when the medium is placed horizontally. For example, the shown sample holder allows the sample to be embedded within the substantially transparent embedding medium in a horizontal direction, perpendicular to the substantially vertical orientation of the optical axis of the detection objective arrangement in upright and inverted microscopes, allowing imaging of transient events in living biological samples.

Sample holder 500 has been formed by molding a substantially transparent material in a cylindrical shape over T-spike rotary mounting 510. In some embodiments, T-spike rotary mounting 510 includes a medical grade Polytetrafluoroethylene material. A sample is placed inside the molded substantially transparent material and sealed to contain the sample within the substantially transparent material even if the molded holder is placed in a horizontal position. The sample and the sample holder may be rotated by rotating the T-spike rotary mounting (e.g., rotation by knob or gear within chamber assembly 400 of FIG. 4 placed under a microscope). Prior sample mounting and sample holder solutions for selective plane light sheet microscopy that exist to date have not been designed to be used with conventional microscope stand. Unlike the embodiments described herein, prior sample mounting methods do not offer fast, efficient, and reproducible results, neither do they guarantee stable sample positioning for the observation and image acquisition. In some embodiments, an embedding medium is formed with sufficient rigidity to withstand manipulating it around a substantially horizontal direction with repeatable sample positioning that greatly alleviates the need for refocusing on the sample.

Figure 6:
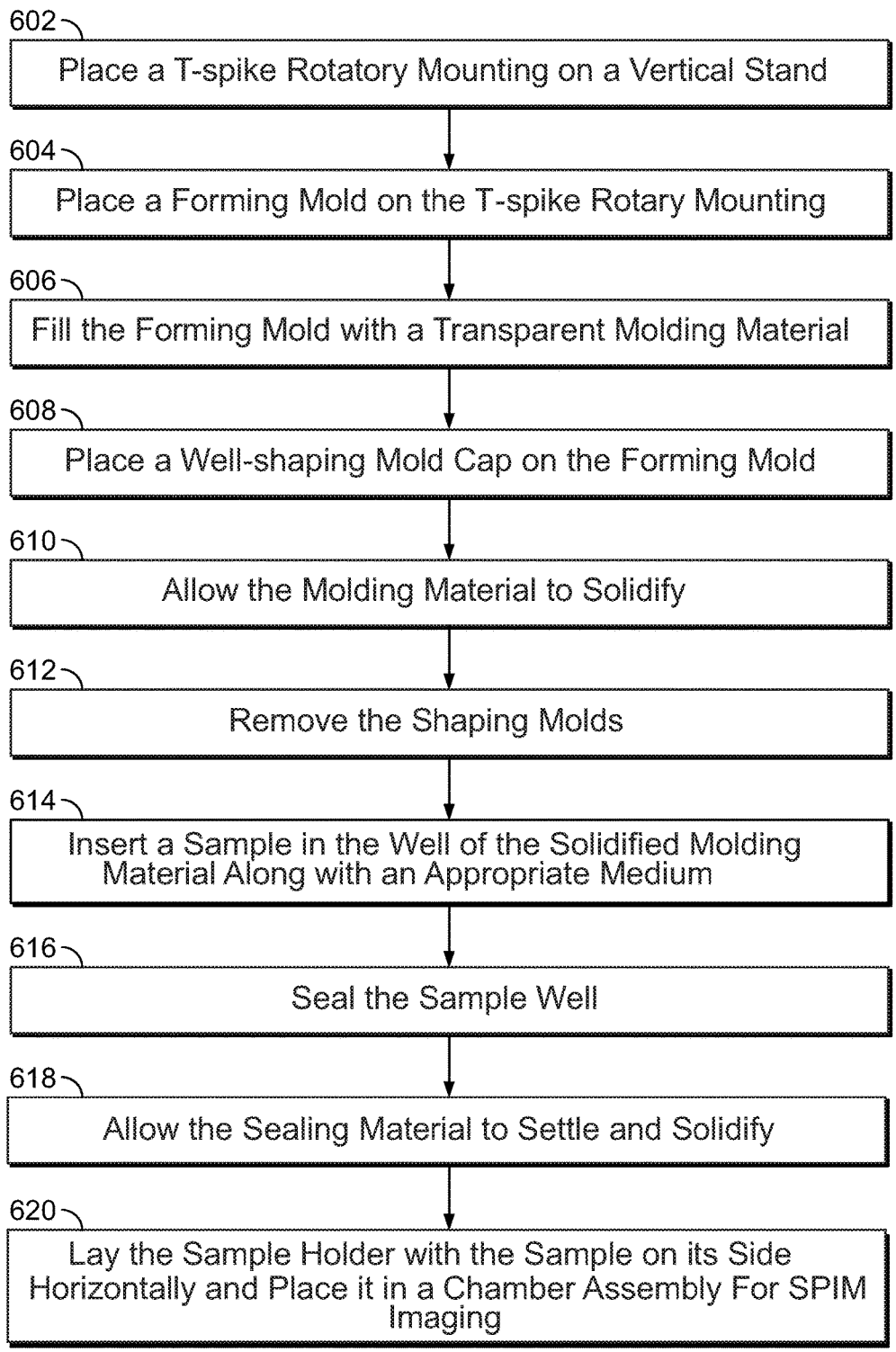
FIG. 6 is a flowchart illustrating an embodiment of a process for forming a molded sample holder.

FIG. 6 is a flowchart illustrating an embodiment of a process for forming a molded sample holder. For example, the process of FIG. 6 is utilized to form sample holder 500 shown in FIG. 5. FIGS. 7A-7H illustrate an embodiment of various steps of forming a molded sample holder.

Figure 7A:
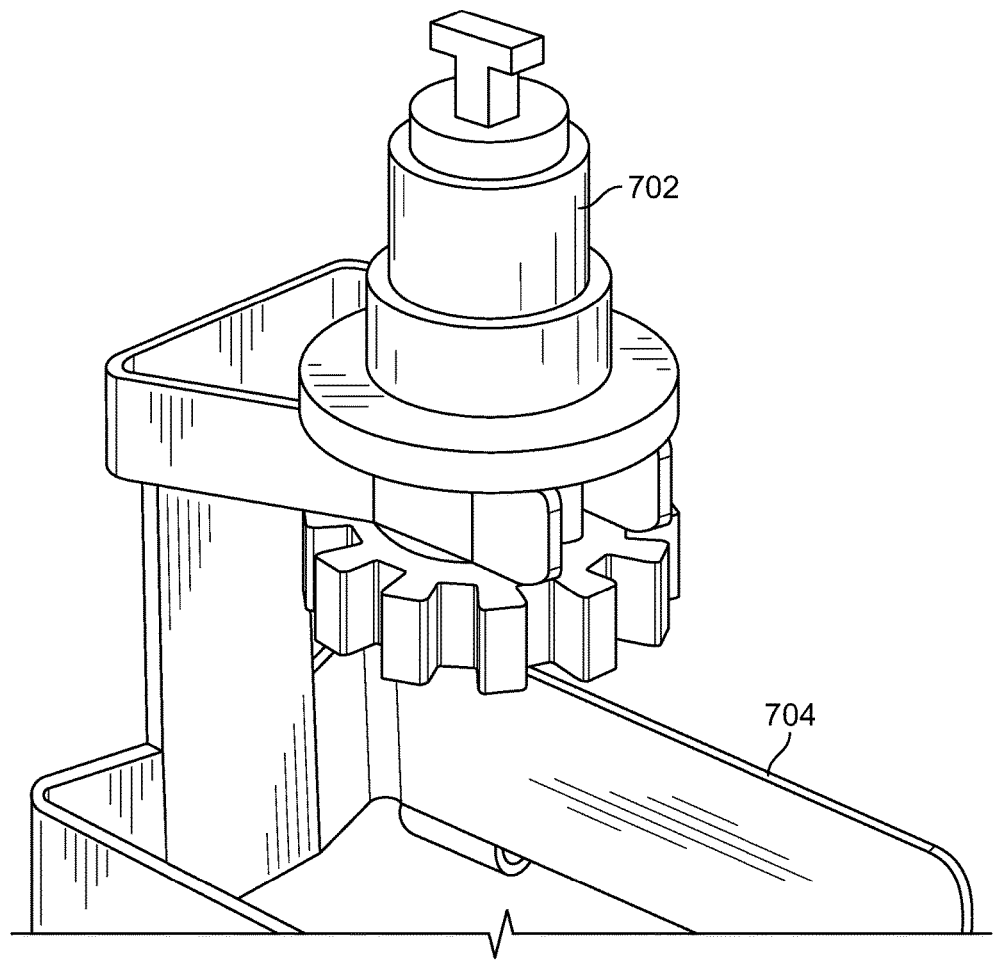
FIG. 7A is an example of the placement of the T-spike rotary mounting 702 on the vertical stand 704.

At 602, a T-spike rotary mounting is placed on a vertical stand. In some embodiments, the T-spike rotary mounting is the rotatory mounting shown in FIG. 5. The vertical holder allows the T-spike rotary mounting to be positioned vertically for the molding process and the mounting is removed from the vertical stand after the molding process for placement inside a chamber of a chamber assembly (e.g., shown in FIG. 4). An example of the placement of the T-spike rotary mounting 702 on the vertical stand 704 is illustrated in FIG. 7A.

Figure 7B:
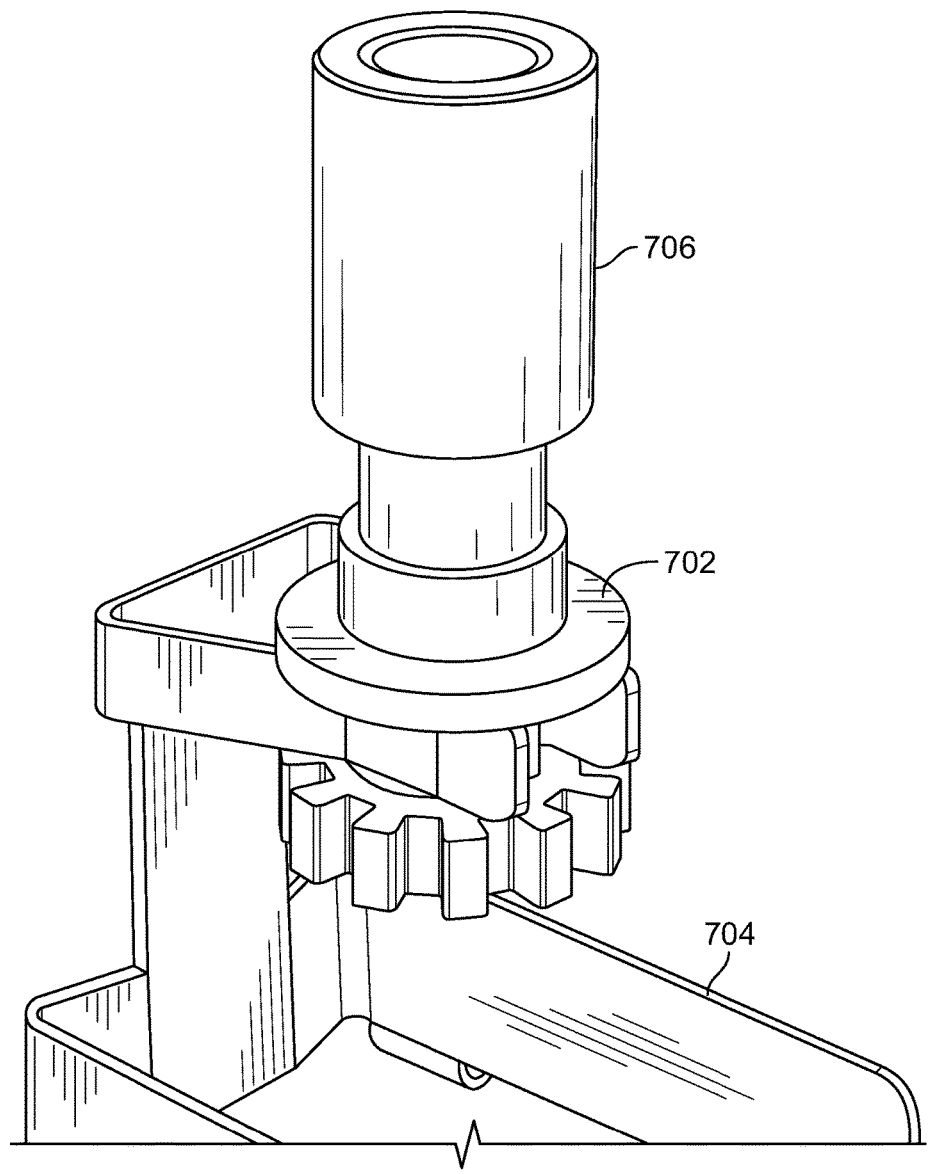
FIG. 7B is an example of the placement of forming mold 706 over T-spike rotary mounting 702.

At 604, a forming mold is placed on the T-spike rotary mounting. For example, the forming mold is a hollow cylinder that can be coupled to the T-spike rotary mounting. The forming mold tightly fits onto the rotary mounting to avoid leakage of any liquid material filled in the forming mold. An example of the placement of forming mold 706 over T-spike rotary mounting 702 is illustrated in FIG. 7B.

Figure 7C:
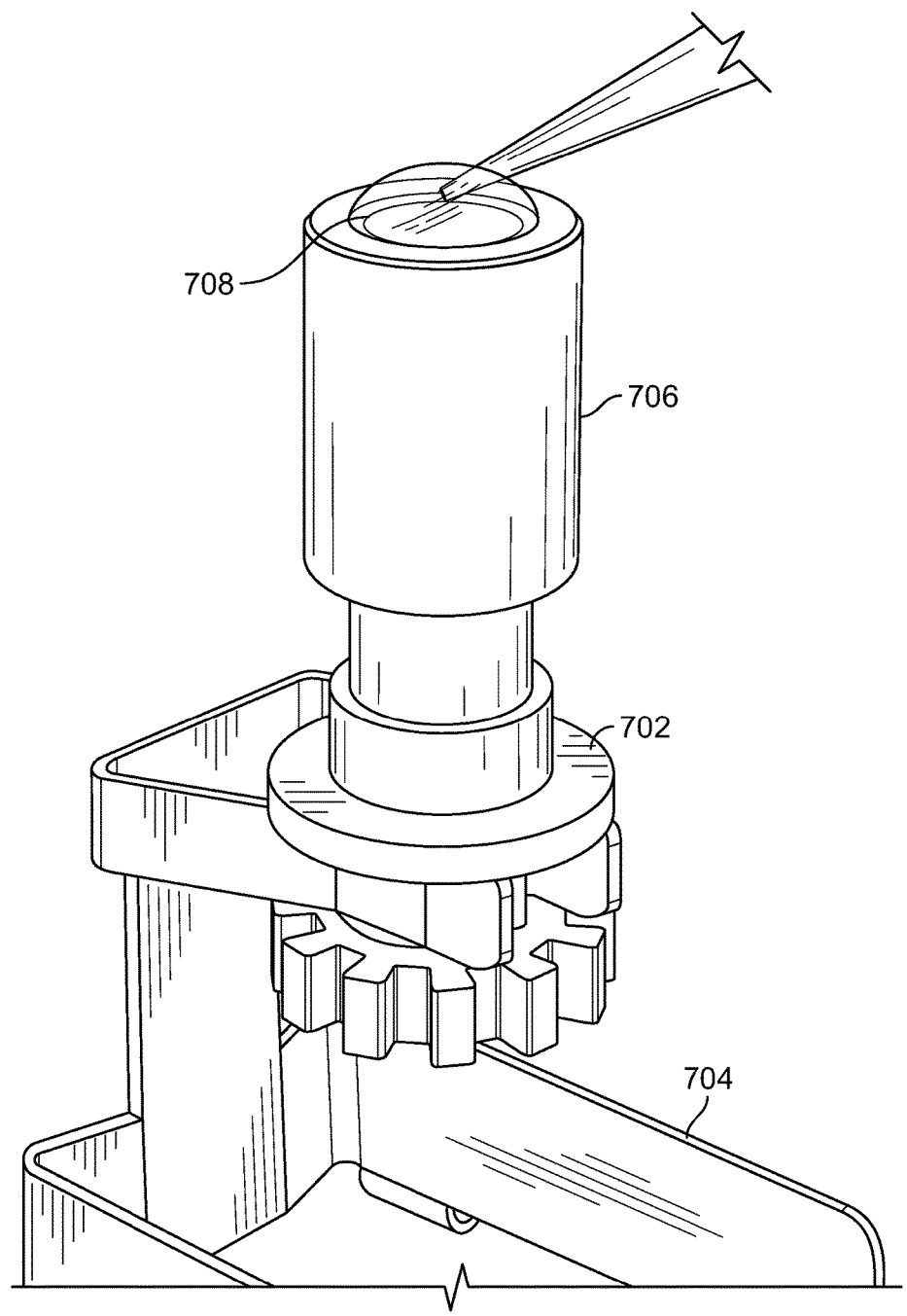
FIG. 7C is an example of the filling of the inside cavity of the forming mold with molding material 708 using a pipette.

At 606, the forming mold is filled with a substantially transparent molding material. The molding material may be initially in a liquid or gel state and will solidify over a period of time to become rigid. Examples of the substantially transparent molding material include agar, agarose, gellan gum, or another gelling agent. For example, a Phytagel solution (e.g., 0.8%) is filled in the forming mold. An example of the filling of the inside cavity of the forming mold with molding material 708 using a pipette is shown in FIG. 7C.

Figure 7D:
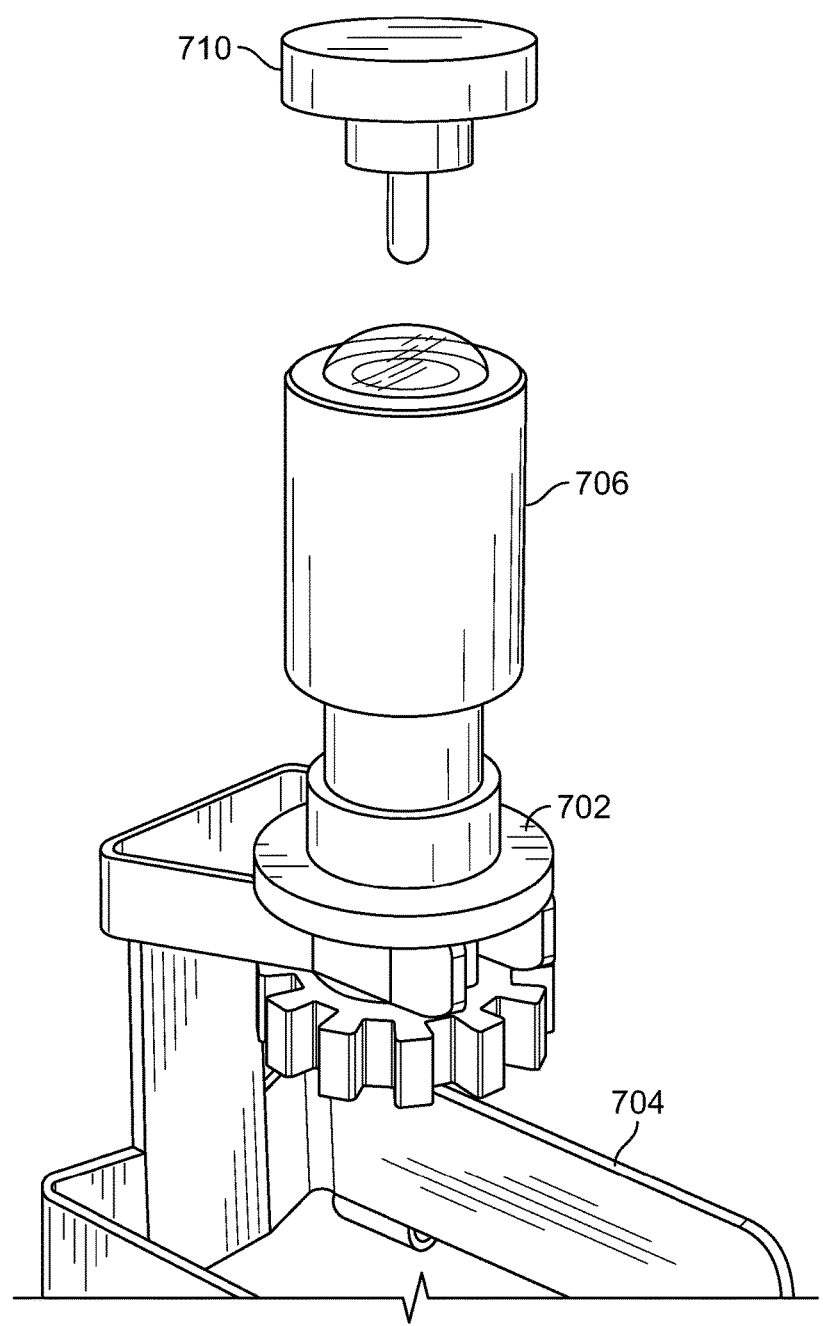
FIG. 7D is an example of capping the forming mold with well-shaping mold cap 710.
Figure 7E:
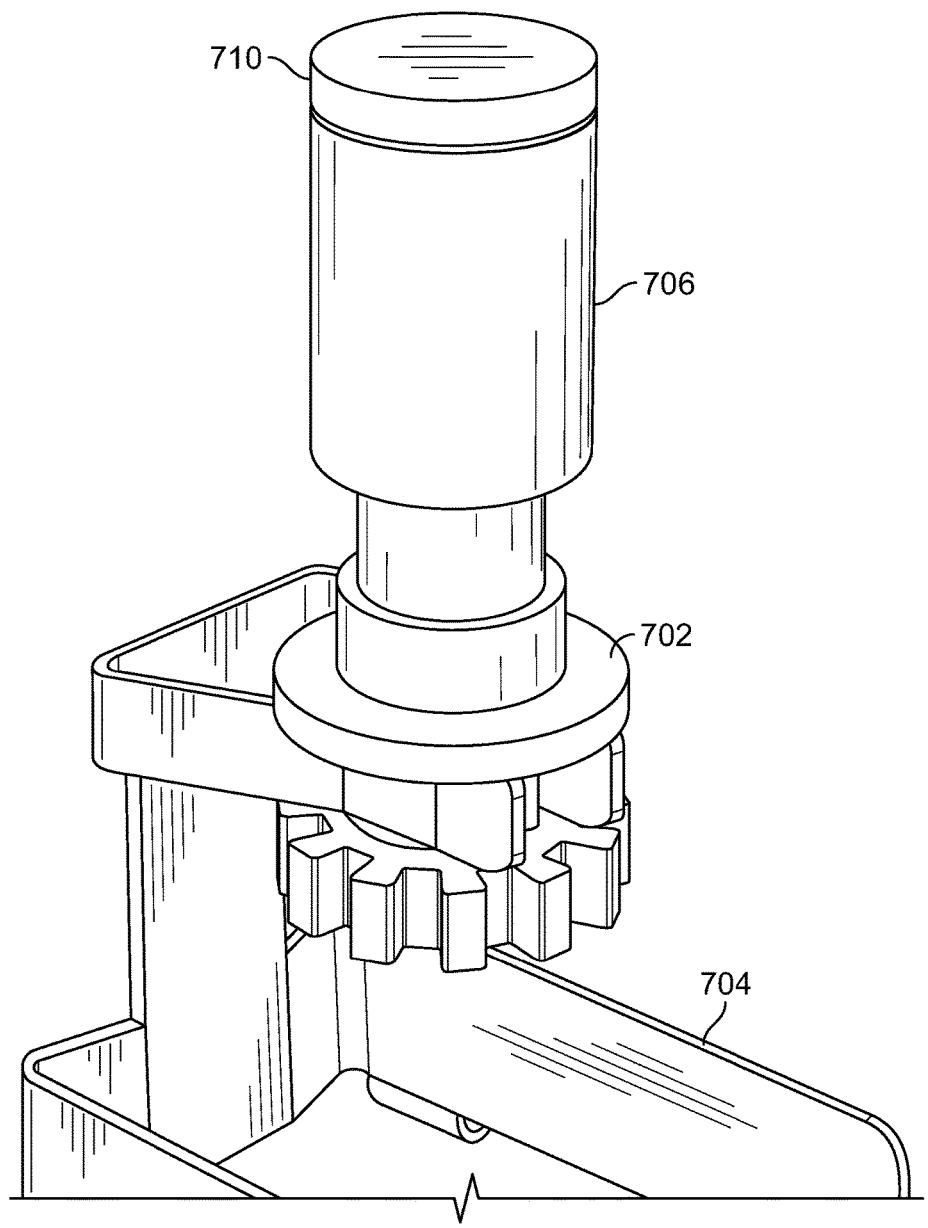
FIG. 7E is an example illustration after capping with well-shaping mold cap 710.

At 608, a well-shaping mold cap is placed on the forming mold. The well-shaping mold cap creates a well in the molding material where a sample can be placed. The shown well-shaping mold cap 710 includes a solid cylindrical extension that is smaller in diameter than the diameter of the interior of the forming mold and when the well-shaping mold cap is capped on the forming mold, the extension of the well-shaping mold cap is inserted inside the forming mold to occupy and form the space of the sample well surrounded by the molding material. For example, the cap has a pin extension that will form a pit at the top of the molding material when the molding material solidifies around the pin. The diameter of the cylinder extension/pin is such to host a biological sample together with the sample's natural medium. The well-shaping mold cap is placed prior to solidification of the molding material. An example of capping the forming mold with well-shaping mold cap 710 is shown in FIG. 7D. An example illustration after capping with well-shaping mold cap 710 is shown in FIG. 7E.

At 610, the molding material is allowed to solidify. For example, at room temperature, a Phytagel molding material solidifies in approximately five minutes and the amount of time required for solidification is allowed to pass.

Figure 7F:
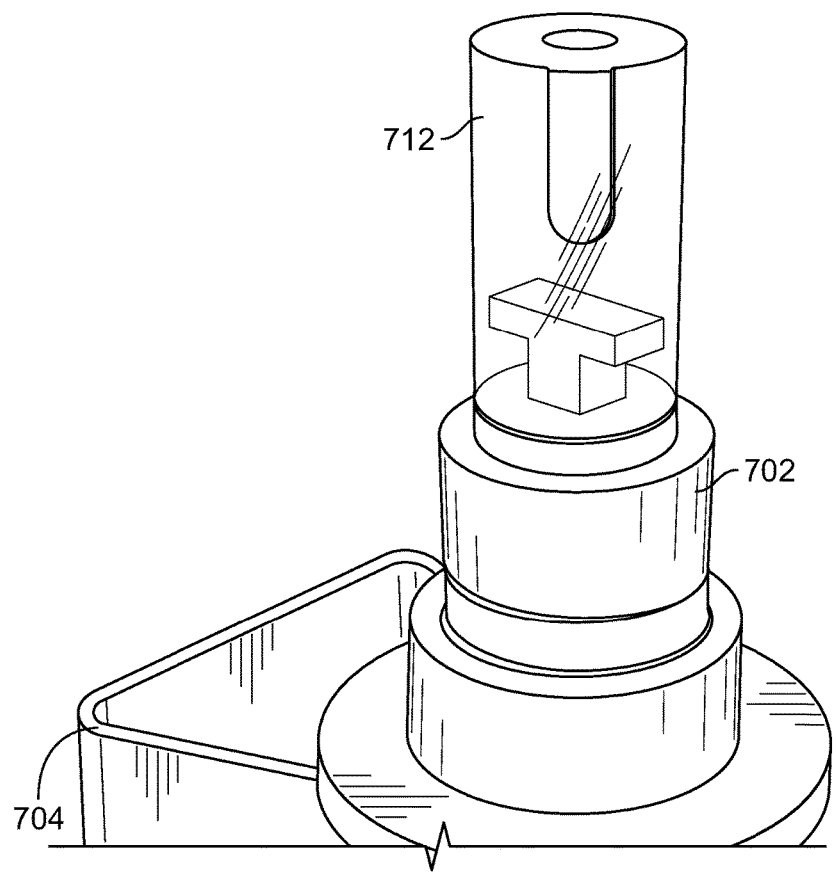
FIG. 7F illustrates an example of the resulting solidified molding material 712.

At 612, the shaping molds are removed. For example, the forming mold and the mold cap are removed. The result is a solidified molding material in the shape of a cylinder with an open top cylindrical interior well. FIG. 7F illustrates an example of the resulting solidified molding material 712.

Figure 7G:
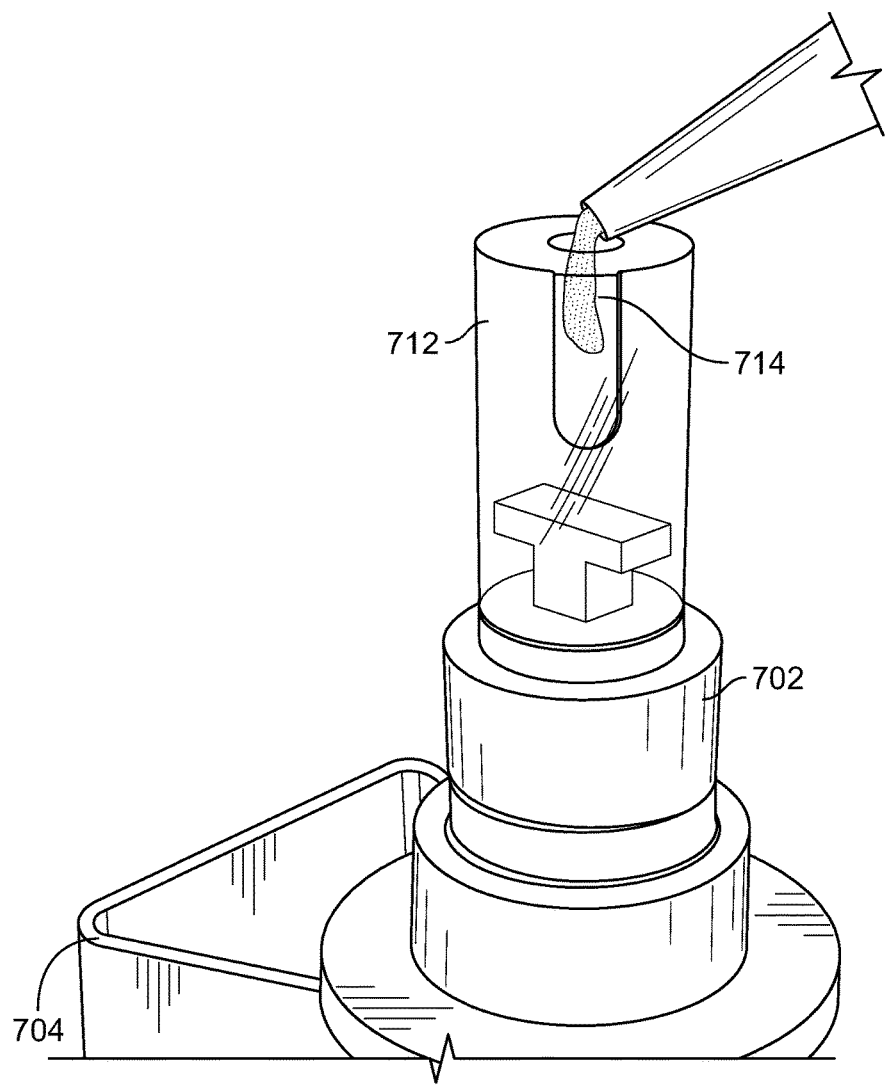
FIG. 7G is an example of the placement of sample 714 suspended in the medium.

At 614, a sample is inserted in the well of the solidified molding material along with an appropriate medium. For example, a biological sample and solution (e.g., solution that is natural, transparent, saline, etc.) is placed inside the well. An example of the placement of sample 714 suspended in the medium is illustrated in FIG. 7G.

Figure 7H:
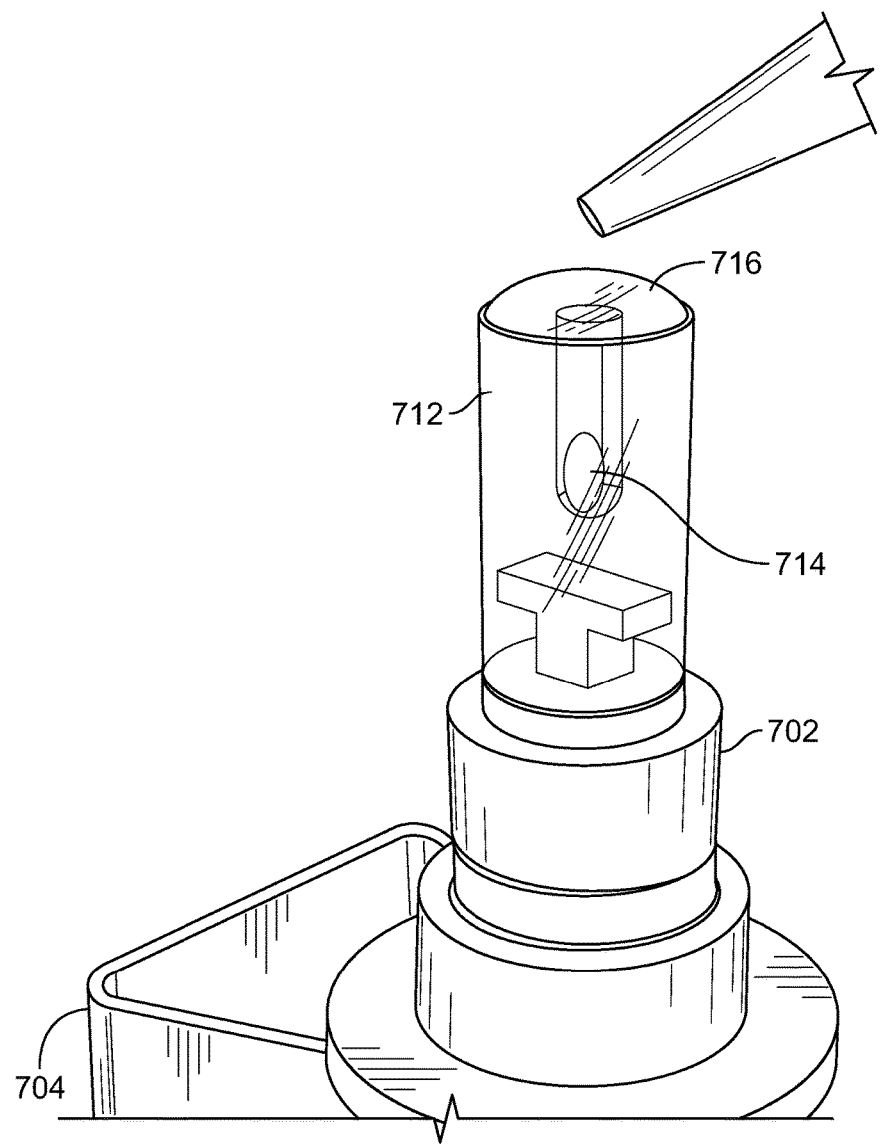
FIG. 7H is an example of sealing the well with sealing material 716.

At 616, the well with the sample is sealed. For example, the well is sealed with a substantially transparent material. The sealing material may be initially in a liquid or gel consistency that solidifies after a period of time. Examples of the sealing material include agar, agarose, gellan gum, or another gelling agent. For example, a low melting agarose gel drop (e.g., 1%) is used as the sealing material and is placed on the opening of the well with the sample. An example of sealing the well with sealing material 716 is illustrated in FIG. 7H.

At 618, the sealing material is allowed to settle and solidify. For example, the agarose drop is allowed to settle and solidify for approximately one minute. By sealing the well, a sample contained in the well does not escape the well even if the well is tipped on its side.

At 620, the sample holder with the sample is laid on its side horizontally placed in a chamber assembly for SPIM imaging. For example, the sample holder and the T-spike rotary mounting is placed in the chamber of chamber assembly 400 of FIG. 4. The chamber assembly may then be placed on the translation stage of the microscope for SPIM imaging.

Figure 8:
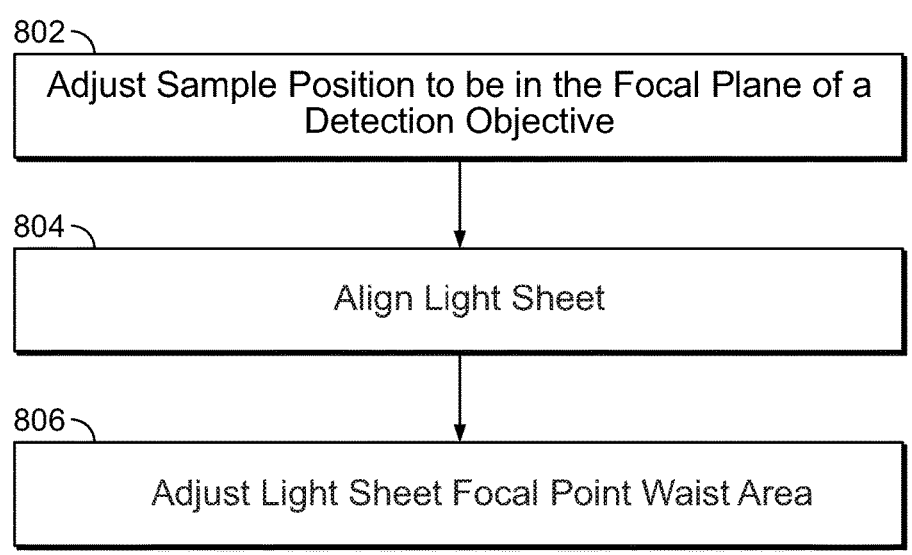
FIG. 8 is a flowchart illustrating an embodiment of a process for aligning a detection plane and illumination plane of a SPIM converted microscope.
Figure 9A:
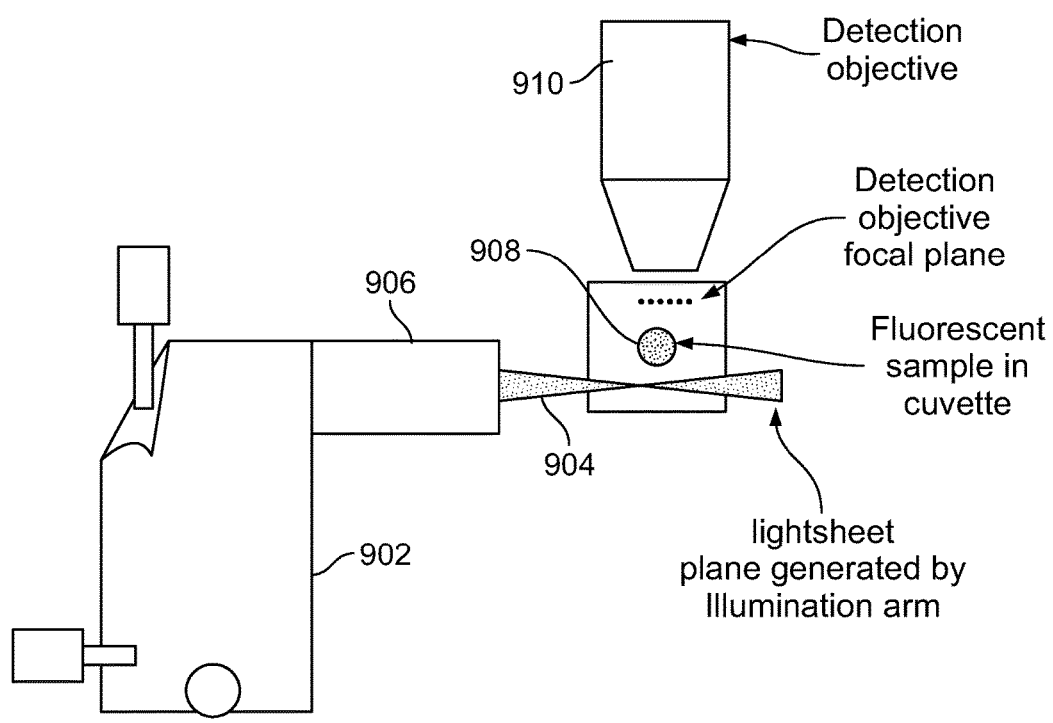
FIG. 9A shows an example diagram of a slide view of the components utilized during the adjustment.

FIG. 8 is a flowchart illustrating an embodiment of a process for aligning a detection plane and illumination plane of a SPIM converted microscope. The alignment allows a sharper image of the sample to be obtained under a SPIM microscope. An example of the system utilized for SPIM is the system shown in FIG. 1B. FIGS. 9A-9E illustrate an example of aligning a detection plane and illumination plane of a SPIM-converted microscope. FIG. 9A shows an example diagram of a slide view of the components utilized during the adjustment. Illumination unit 902 outputs light sheet 904 via illumination objective 906. Sample 908 is to be detected via detection objective 910. As shown in FIG. 9A, the light sheet plane and the detection objective focal plane are not on the sample and not synchronized with each other.

Figure 9B:
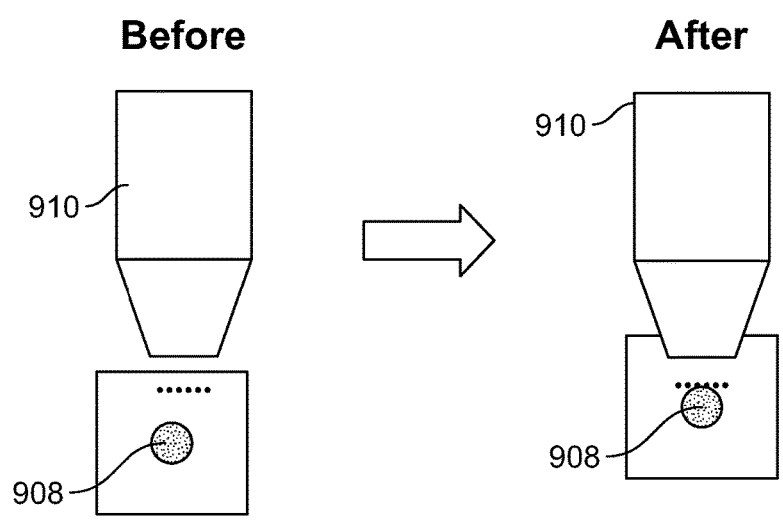
FIG. 9B shows an example diagram of a slide view of before and after diagrams of aligning the detection objective focal plane with the sample.

At 802, sample position is adjusted to be in the focal plane of a detection objective. Adjusting the sample position may include adjusting a position of the sample and/or focal point of a detection objective of the microscope. For example, the laser light from the illumination arm is turned off and the transmitted light from the microscope stand is turned on. Then the sample is placed into focus of the detection objective by moving the X, Y, and Z adjustments on the stand holding the sample. If the microscope is not equipped with transmitted light, brightfield illumination (e.g., a condenser is not necessary) may be utilized. The focus may be set on the first surface (or very close to it, within the sample) to avoid the transparency of the sample affecting the adjustment. FIG. 9B shows an example diagram of a slide view of before and after diagrams of aligning the detection objective focal plane with the sample.

Figure 9C:
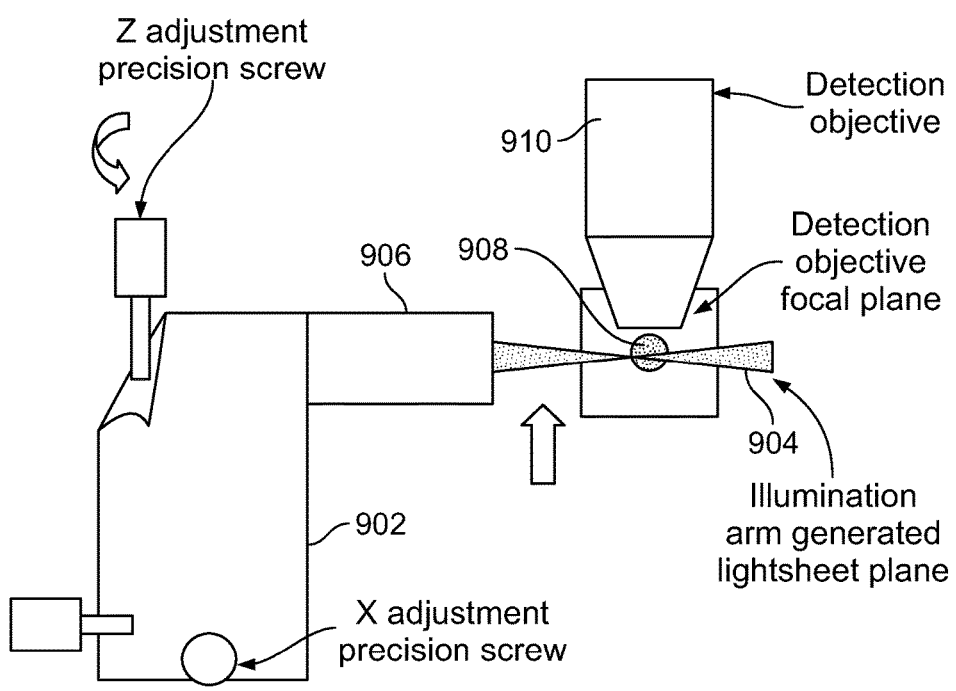
FIG. 9C shows an example diagram of a slide view of aligning the light sheet with the detection objective focal plane.
Figure 9D:
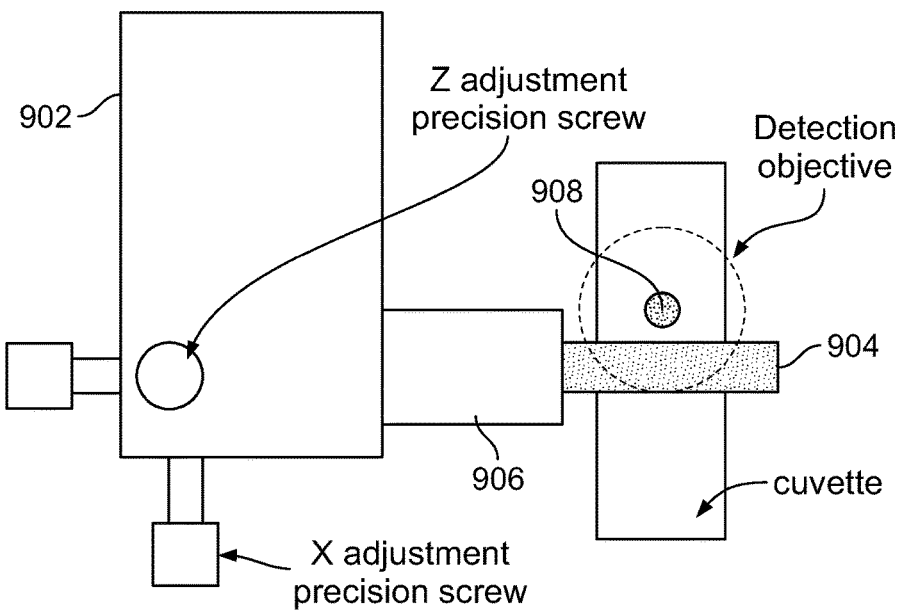
FIG. 9D shows an example diagram of a top view of before and after diagrams of aligning the light sheet with the detection objective focal plane.
Figure 9D:
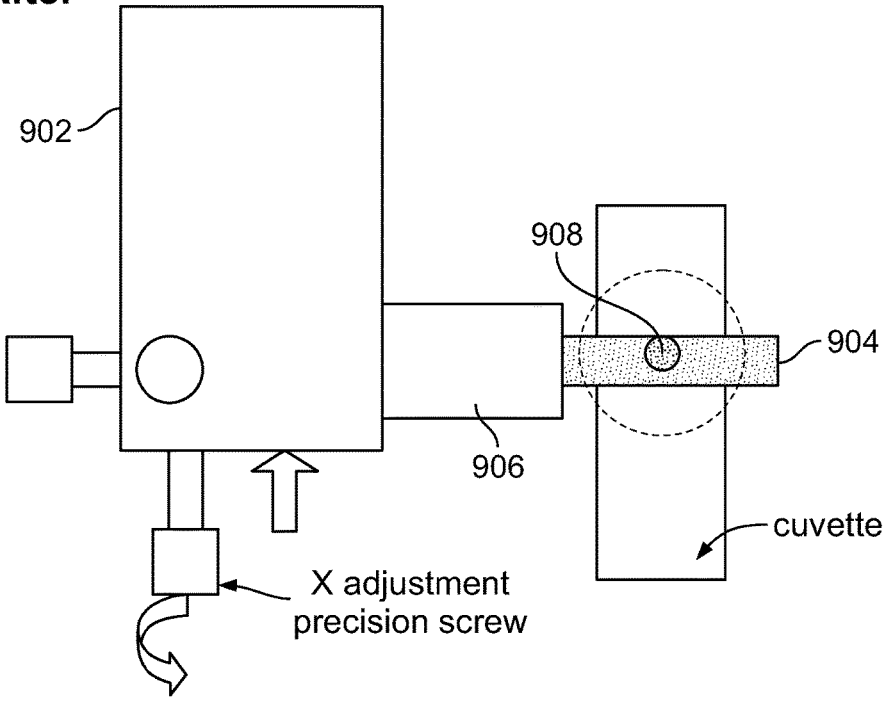

At 804, the light sheet is aligned. For example, transmitted light illumination is turned off and the laser illumination is turned on. Aligning the light sheet includes adjusting the height of the laser beam to illuminate the focal plane of the detection objective. This may include adjusting the X and Z position of the light source to align the light sheet of the light source with the focal plane of the detection objective. If more than one illumination source is utilized, any additional illumination source is adjusted to alight its light sheet with the focal plane. FIG. 9C shows an example diagram of a slide view of aligning the light sheet with the detection objective focal plane. FIG. 9D shows an example diagram of a top view of before and after diagrams of aligning the light sheet with the detection objective focal plane.

Figure 9E:
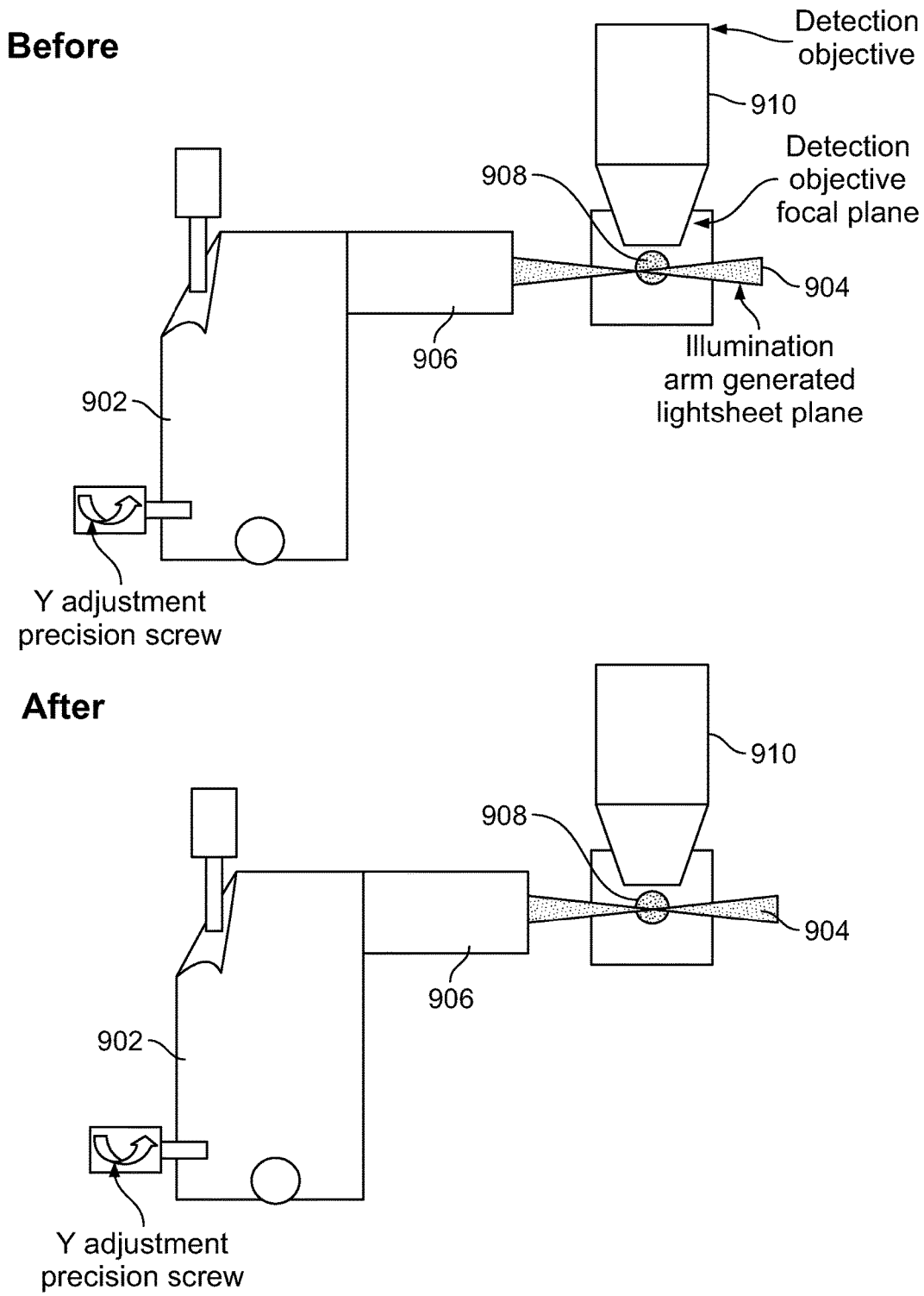
FIG. 9E shows an example diagram of a top view of before and after diagrams of aligning the focal point/waist of the light sheet to the area of interest.

At 806, the light sheet focal point area is adjusted. The light sheet focal point (i.e., waist) is adjusted to be on the area of interest of the sample. For example, the Y position of the light sheet is adjusted on the illumination unit at the center of the sample in the field of view of the microscope. If more than one illumination source is utilized, any additional illumination source is adjusted to align the focal point of its light sheet with the center of the field of view. FIG. 9E shows an example diagram of a top view of before and after diagrams of aligning the focal point/waist of the light sheet to the area of interest.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for holding a sample for a microscope, comprising:
    a first container with a substantially transparent wall; and
    a second container formed from a substantially transparent embedding medium molded on a mounting, wherein the second container is configured to enclose the sample and at least a portion of the second container is positioned within the first container;
    wherein the second container is configured to be rotated at least in part within the first container about a rotational axis and configured to be placed within a detection optical path of an optical detection axis of the microscope.

2. The system of claim 1, wherein the second container is positioned horizontally within the first container.

3. The system of claim 1, wherein the rotational axis is substantially perpendicular to the optical detection axis of the microscope.

4. The system of claim 3, wherein the optical detection axis of the microscope is vertical.

5. The system of claim 1, wherein the first container has a top opening.

6. The system of claim 1, wherein at least a portion of a bottom of the first container is substantially transparent.

7. The system of claim 1, wherein the substantially transparent embedding medium includes a solidified gelling agent.

8. The system of claim 1, wherein the sample enclosed in the second container includes a biological sample suspended in a substantially transparent liquid.

9. The system of claim 1, wherein the first container is filled with a solution for a water immersion objective of the microscope.

10. The system of claim 1, wherein the microscope is configured to perform selective plane illumination microscopy.

11. A method for forming a holding well for a microscopy sample, comprising:
    filling a body forming mold with a substantially transparent molding solution;
    inserting at least a portion of a well-shaping mold into the body forming mold holding the substantially transparent molding solution;
    allowing the molding solution to solidify;
    removing the body forming mold and the well-shaping mold;
    inserting the microscopy sample in the holding well formed in the solidified molding solution by the well-shaping mold; and
    sealing the holding well.

12. The method of claim 11, wherein the substantially transparent molding solution includes a gelling agent.

13. The method of claim 11, wherein filling the body forming mold with the substantially transparent molding solution includes filling the substantially transparent molding solution in a cavity of the body forming mold enclosed at least in part by a removable mounting.

14. The method of claim 11, wherein the body forming mold includes a cylindrical cavity.

15. The method of claim 11, wherein the solidified molding solution has been molded over an extension of a mounting.

16. The method of claim 15, wherein the mounting is configured to rotate the solidified molding solution during examination of the microscopy sample under a microscope.

17. The method of claim 11, wherein the microscopy sample is sealed within the sample holding well formed by the solidified substantially transparent molding solution and a seal of the holding well.

18. The method of claim 11, wherein sealing the holding well includes applying a liquid or gel sealing solution on an opening of the sample holding well and allowing the sealing solution to solidify.

19. The method of claim 11, wherein sealing the holding well includes applying an agarose gel on an opening of the holding well.

20. The method of claim 11, further comprising tilting the formed mold horizontally for selective plane illumination microscopy.

* * * * *